(12) United States Patent
Jones

(10) Patent No.: US 6,395,532 B1
(45) Date of Patent: May 28, 2002

(54) MODIFIED ENZYMES AND THEIR USE FOR PEPTIDE SYNTHESIS

(75) Inventor: J. Bryan Jones, 1275 Seaforth Crescent, RR 3, Lakefield, Ontario (CA), K0L 2H0

(73) Assignees: Genencor International, Inc., Rochester, NY (US); J. Bryan Jones, Lakefield (CA)

( * ) Notice: Subject to any disclaimer, the term of this patent is extended or adjusted under 35 U.S.C. 154(b) by 0 days.

(21) Appl. No.: 09/234,957

(22) Filed: Jan. 21, 1999

Related U.S. Application Data

(60) Provisional application No. 60/072,351, filed on Jan. 23, 1998, and provisional application No. 60/072,265, filed on Jan. 23, 1998.

(51) Int. Cl.$^7$ .............................. C12N 9/56; C12N 9/14; C12N 9/16; C07H 21/04
(52) U.S. Cl. ........................ 435/222; 435/195; 435/196; 435/230; 435/252.3; 435/320.1; 435/440; 435/264; 435/832; 435/836; 530/350; 536/23.2
(58) Field of Search ................................. 435/196, 195, 435/230, 252.3, 320.1, 222, 264; 530/350; 536/23.2

(56) References Cited

U.S. PATENT DOCUMENTS

| | | | |
|---|---|---|---|
| 5,208,158 A | 5/1993 | Bech et al. | 435/219 |
| 5,244,791 A | 9/1993 | Estell | 435/68.1 |
| 5,316,935 A | 5/1994 | Arnold et al. | 435/222 |
| 5,316,941 A | 5/1994 | Estell et al. | 435/252.3 |
| 5,403,737 A | 4/1995 | Abrahmsen et al. | 435/252.3 |
| 5,629,173 A | 5/1997 | Abrahmsen et al. | 435/68.1 |

FOREIGN PATENT DOCUMENTS

| | | |
|---|---|---|
| EP | 0 328 229 A1 | 8/1989 |
| WO | WO 91/16423 | 10/1991 |
| WO | WO 96/27671 | 9/1996 |

OTHER PUBLICATIONS

Berglund et al. [J. Am. Chem Soc. 1997 (May 14, 1997), 119 : 5265–66].*
Morihara et al., "α–Chymotrypsin as the Catalyst for Peptide Synthesis," Biochem. J. , 163:531–42 (1977).
West et al., "Enzymes as Synthetic Catalysts: Mechanistic and Active–Site Considerations of Natural and Modified Chymotrypsin," J. Am. Chem. Soc., 112:5313–20 (1990).
West et al., Enzyme–catalyzed Synthesis of Peptides Containing D–Amino Acids, J. Chem. Soc., Chem. Commun., pp 417–18 (1986).
West et al., "Enzyme–Catalyzed Irreversible Formation of Peptides Containing D–Amino Acids," J. Org. Chem., 51:2728–35 (1986).
West et al., "Modification of Proteases to Esterases for Peptide Synthesis: Methylchymotrypsin," J. Am. Chem. Soc., 110:3709–10 (1988).
Zhang et al., Protease–catalyzed Small Peptide Synthesis in Organic Media, Enzyme Microb. Technol., 19:538–44 (1996).
Chen et al., "Incorporation of Unnatural Amino Acid Derivatives into a Peptide Bond via an Oxime Ester Catalyzed By Papain or Lipase," Chem. Commun., 165–66 (1996).
So et al., "Lipase–Catalyzed Synthesis of Peptides Containing D–Amino Acid," Enzyme Microb. Technol., 23:211–15 (1998).
Margolin et al., "Peptide Synthesis Catalyzed by Lipases in Anhydrous Organic Solvents," J. Am. Chem. Soc., 109:3802–04 (1987).
Barbas et al., "Papain Catalyzed Peptide Synthesis: Control of Amidase Activity and the Introduction of Unusual Amino Acids," J. Chem. Soc., Chem. Commun., pp 533–34 (1987).
Kato et al., "First Stereoselective Synthesis of D–Amino Acid N–Alkyl Amide Catalyzed by D–Aminopeptidase," Tetrahedron, 45(18) 5743–54 (1989).
Ekberg et al., "Enzymatic Coupling of Two D–Amino Acid Residues in Aqueous Media," Tetrahedron Letters, 30(5):583–86 (1989).
Abrahmsén et al., "Engineering Subtilisin and Its Substrates for Efficient Ligation of Peptide Bonds in Aqueous Solution, "Biochemistry, 30:4151–59 (1991).
Bonneau et al., "Alteration of the Specificity of Subtilisin BPNé by Site–Directed Mutagenesis in its $S_1$ and $S_1$' Binding Sites," J. Am. Chem. Soc., 113:1026–30 (1991).
Graycar et al, "Altering the Proteolytic Activity of Subtilisin through Protein Engineering," Annals New York Academy of Sciences, 672:71–79 (1992).
Grøn et al., "Extensive Comparison of the Substrate Preferences of Two Subtilisins As Determined with Peptide Substrates Which Are Based on the Principle of Intramolecular Quenching," Biochemistry, 31(26):6011–18 (1992).
Moree et al., "Exploitation of Subtilisin BPNé as Catalyst for the Synthesis of Peptides Containing Noncoded Amino Acids, Peptide Mimetics and Peptides Conjugates," J. Am. Chem. Soc., 119:3942–47 (1997).

(List continued on next page.)

Primary Examiner—Ponnathapu Achutamurthy
Assistant Examiner—Tekchand Saidha
(74) Attorney, Agent, or Firm—McCutchen, Doyle, Brown & Enersen, LLP

(57) ABSTRACT

The present invention relates to modified enzymes with one or more amino acid residues from an enzyme being replaced by cysteine residues, where at least some of the cysteine residues are modified by replacing thiol hydrogen in the cysteine residue with a thiol side chain to form a modified enzyme, wherein the modified enzyme has high esterase and low amidase activity. Also, a method of producing the modified enzymes is provided. The present invention also relates to a method for using the modified enzymes in peptide synthesis.

19 Claims, 8 Drawing Sheets

OTHER PUBLICATIONS

Sears et al., "Engineering Subtilisin for Peptide Coupling: Studies on the Effects of Counterions and Site–Specific Modifications on the Stability and Specificity of the Enzyme," *J. Am. Chem. Soc.*, 116:6521–30 (1994).

Barbas et al., "A Search for Peptide Ligase: Cosolvent–Mediated Conversion of Proteases to Esterases for Irreversible Synthesis of Peptides," *J. Am. Chem. Soc.*, 110:5162–66 (1988).

Chen et al., "Kinetically Controlled Peptide Bond Formation in Anhydrous Alcohol Catalyzed by the Industrial Protease Alcalase," *J. Org. Chem.*, 57:6960–65 (1992).

Chen et al., "Probing the S–1é Subsite Selectivity of an Industrial Alkaline Protease in Anhydrous t–Butanol," *Bioorganic & Medicinal Chemistry Letters*, 3(4):727–33 (1993).

Jönsson et al., "Temperature Effects on Protease Catalyzed Acyl Transfer Reactions in Organic Media," *Journal of Molecular Catalysis B: Enzymatic*, 2:43–51 (1996).

Kawashiro et al., "Effect of Ester Moiety of Substrates on Enantioselectivity of Protease Catalysis in Organic Media," *Biotechnology Letters*, 18(12):1381–86 (1996).

Margolin et al., "Incorporation of D–Amino Acids into Peptides via Enzymatic Condensation in Organic Solvents," *J. Am. Chem. Soc.*, 109:7885–87 (1987).

Stepanov, "Proteinases as Catalysts in Peptide Synthesis," *Pure & Appl. Chem.*, 68(6):1335–39 (1996).

Wong et al., "Enzymes in Organic Synthesis: Use of Subtilisin and a Highly Stable Mutant Derived from Multiple Site–Specific Mutations," *J. Am. Chem. Soc.*, 112:945–53 (1990).

Nakatsuka et al., "Peptide Segment Coupling Catalyzed by the Semisynthetic Enzyme Thiolsubtilisin," *J. Am. Chem. Soc.*, 109:3808–10 (1987).

Sears et al., "Engineering Enzymes for Bioorganic Synthesis: Peptide Bond Formation," *Biotechnolo. Prog.*, 12:423–33 (1996).

Watanabe et al., "A Unique Enzyme from Saccharothrix sp. Catalyzing D–Amino Acid Transfer," *Biochimica et Biophysica Acta*, 1337:40–46 (1997).

Berglund et al., "Altering the Specificity of Subtilisin *B. lentus* by Combining Site–Directed Mutagenesis and Chemical Modification," *Bioorganic & Mechanical Chemistry Letters*, 6:2507–2512 (1996).

Bech et al., "Chemical Modifications of a Cysteinyl Residue Introduced in the Binding Site of Carboxypeptidase Y by Site–Directed Mutagenesis," *Carlsberg Res. Commun.*, 53:381–393 (1988).

Wynn et al., "Chemical Modification of Protein Thiols: Formation of Mixed Disulfides," *Methods in Enzymology*, 251:351–356 (1995).

Gloss et al., "Examining the Structural and Chemical Flexibility of the Active Site Base, Lys–258, of *Escherichia coli* Aspartate Aminotransferase by Replacement with Unnatural Amino Acids," *Biochemistry*, 34:12323–12332 (1995).

Wynn et al., "Mobile Unnatural Amino Acid Side Chains in the Core of Staphylococcal Nuclease," *Protein Science*, 5:1026–1031 (1996).

Berglund et al., "Chemical Modification of Cysteine Mutants of Subtilisin *Bacillus lentus* Can Create Better Catalysts Than The Wild–Type Enzyme," *J. Am. Chem. Soc.*, 119:5265–5266 (1997).

Gron et al., "A Highly Active and Oxidation–Resistant Subtilisin–Like Enzyme Produced by a Combination of Site–Directed Mutagenesis and Chemical Modification," *Eur. J. Biochem.*, 194:897–901 (1990).

Bech et al., "Significance of Hydrophobic $S_4$–$P_4$ Interactions in Subtilisin 309 from *Bacillus lentus*," *Biochemistry*, 32:2847–2852 (1993).

Wynn et al., "Unnatural Amino Acid Packing Mutants of *Escherichia coli* Thioredoxin Produced by Combined Mutagenesis/Chemical Modification Techniques," *Protein Science*, 2:395–403 (1993).

Wynn et al., "Comparison of Straight Chain and Cyclic Unnatural Amino Acids Embedded in the Core of Staphylococcal Nuclease," *Protein Science*, 6:1621–1626 (1997).

Kawase et al., "Effect of Chemical Modification of Tyrosine Residues on Activities of Bacterial Lipase," *Journal of Fermentation and Bioengineering*, 72:317–319 (1991).

Raia et al., "Activation of *Sulfolobus Solfataricus* Alcohol Dehydrogenase by Modification of Cysteine Residue 38 with Iodoacetic Acid," *Biochemistry*, 35:638–647 (1996).

Ramachandran et al., "Stabilization of Barstar by Chemical Modification of the Buried Cysteines," *Biochemistry*, 35:8776–8785 (1996).

Davies et al., "A Semisynthetic Metalloenzyme Based on a Protein Cavity That Catalyzes the Enantiosleective Hydrolysis of Ester and Amide Substrates," *J. Am. Chem. Soc.*, 119:11643–11652 (1997).

Polgar et al., "A New Enzyme Containing a Synthetically Formed Active Site. Thiol–Subtilisin," *Journal of American Chemical Society*, 88:3153–3154 (1966).

Stewart et al., "Catalytic Oxidation of Dithiols by a Semisynthetic Enzyme," *J. Am. Chem. Soc.*, 108:3480–3483 (1986).

Radziejewski et al., "Catalysis of N–Alkyl–1,4–Dihydronicotinamide Oxidation by a Flavopapain: Rapid Reaction in All Catalytic Steps," *J. Am. Chem. Soc.*, 107:3352–3354 (1985).

Hilvert et al., "A Highly Active Thermophilic Semisynthetic Flavoenzyme," *J. Am. Chem. Soc.*, 110:682–689 (1988).

Hilvert et al., "New Semisynthetic Flavoenzymes Based on a Tetrameric Protein Template, Glyceraldehyde–3–Phosphate Dehydrogenase," *J. Am. Chem. Soc.*, 107:5805–5806 (1985).

Rokita et al., "Synthesis and Characterization of a New Semisynthetic Enzyme, Flavolysozyme," *J. Am. Chem. Soc.*, 108:4984–4987 (1986).

Kokubo et al., "Flavohemoglobin: A Semisynthetic Hydroxylase Acting in the Absence of Reductase," *J. Am. Chem. Soc.*, 109:606–607 (1987).

Suckling et al., "Carbon–Carbon Bond Formation Mediated by Papain Chemically Modified by Thiazolium Salts," *Bioorganic & Medicinal Chemistry Letters*, 3:531–534 (1993).

Di Bello, "Total Synthesis of Proteins by Chemical Methods: The Horse Heart Cytochrome C Example," *Gazzetta Chimica Italiana*, 126:189–197 (1996).

O'Connor et al., "Probing an Acyl Enzyme of Selenosubtilisin by Raman Spectroscopy," *J. Am. Chem. Soc.*, 118:239–240 (1996).

Peterson et al., "Nonessential Active Site Residues Modulate Selenosubtilisin's Kinetic Mechanism," *Biochemistry*, 34:6616–6620 (1995).

Bell et al., "Kinetic Studies on the Peroxidase Activity of Selenosubtilisin," *Biochemistry*, 32:3754–3762 (1993).

Peterson et al., "Selenosubtilisin's Peroxidase Activity Does Not Require an Intact Oxyanion Hole," *Tetrahedron*, 53:12311–12317 (1997).

Wu et al., "Conversion of a Protease into an Acyl Transferase: Selenolsubtilisin," *J. Am. Chem. Soc.*, 111:4514–4515 (1989).

House et al., "$^1$H NMR Spectroscopic Studies of Selenosubtilisin," *Biochemistry*, 32:3468–3473 (1993).

Valenzuela et al., "Kinetic Properties of Succinylated and Ethylenediamine–Amidated δ–Chymotrypsins," *Biochim. Biophys. Acta*, 250:538–548 (1971).

Siddiqui et al., "Arthrobacter D–Xylose Isomerase: Chemical Modification of Carboxy Groups and Protein Engineering of pH Optimum," *Biochem. J.*, 295:685–691 (1993).

Kuang et al., "Enantioselective Reductive Amination of α–Keto Acids to α–Amino Acids by a Pyridoxamine Cofactor in A Protein Cavity," *J. Am. Chem. Soc.*, 118:10702–10706 (1996).

White et al., "Sequential Site–Directed Mutagenesis and Chemical Modification to Convert the Active Site Arginine 292 Of Aspartate Aminotransferase to Homoarginine," *Journal of the American Chemical Society*, 114:292–293 (1992).

Engler et al., "Critical Functional Requirement for the Guanidinium Group of the Arginine 41 Side Chain of Human Epidermal Growth Factor as Revealed by Mutagenic Inactivation and Chemical Reactivation," *The Journal of Biological Chemistry*, 267:2274–2281 (1992).

Planas et al., "Reengineering the Catalytic Lysine of Aspartate Aminotransferase by Chemical Elaboration of a Genetically Introduced Cysteine," *Biochemistry*, 30:8268–8276 (1991).

Smith et al., "An Engineered Change in Substrate Specificity of Ribolosebisphosphate Carboxylase/Oxygenase," *The Journal of Biological Chemistry*, 265:1243–1245 (1990).

Smith et al., "Subtle Alteration of the Active Site of Ribulose Bisphosphate Carboxylase/Oxygenase by Concerted Site–Directed Mutagenesis and Chemical Modification," *Biochemical and Biophysical Research Communications*, 152:579–584 (1988).

Smith et al., "Restoration of Activity to Catalytically Deficient Mutants of Ribulosebisphosphate Carboxylase/Oxygenase by Aminoethylation," *The Journal of Biological Chemistry*, 263:4921–4925 (1988).

Kanaya et al., "Role of Cysteine Residues in Ribonuclease H from *Escherichia coli*," *Biochem. J.*, 271:59–66 (1990).

Xu et al., "Amino Acids Lining the Channel of the γ–Aminobutyric Acid Type A Receptor Identified by Cysteine Substitution," *The Journal of Biological Chemistry*, 268:21505–21508 (1993).

Svensson et al., "Mapping the Folding Intermediate of Human Carbonic Anhydrase II. Probing Substructure by Chemical Reactivity and Spin and Fluorescence Labeling of Engineered Cysteine Residues," *Biochemistry*, 34:8606–8620 (1995).

Akabas et al., "Acetylcholine Receptor Channel Structure Probed in Cysteine–Substitution Mutants," *Science*, 258:307–310 (1992).

Liu et al., "Site–Directed Fluorescence Labeling of P–Glycoprotein on Cysteine Residues in the Nucleotide Binding Domains," *Biochemistry*, 35:11865–11873 (1996).

Frillingos et al., "Cysteine–Scanning Mutagenesis of Helix II and Flanking Hydrophilic Domains in the Lactose Permease of *Escherichia coli*," *Biochemistry*, 36:269–272 (1997).

Kirley, "Reduction and Fluorescent Labeling of Cyst(e)ine–Containing Proteins for Subsequent Structural Analyses," *Analytical Biochemistry*, 180:231–236 (1989).

Buckwalter et al., "Improvement in the Solution Stability of Porcine Somatotropin by Chemical Modification of Cysteine Residues," *J. Agric. Food Chem.*, 40:356–362 (1992).

Nishimura et al., "Reversible Modification of the Sulfhydryl Groups of *Escherichia coli* Succinic Thiokinase with Methanethiolating Reagents, 5,5'–Dithio–bis(2–Nitrobenzoic Acid), p–Hydroxymercuribenzoate, and Ethylmercurithiosalicylate," *Archives of Biochemistry and Biophysics*, 170:461–467 (1975).

Lewis et al., "Determination of Interactive Thiol Ionizations in Bovine Serum Albumin, Glutathione, and Other Thiols by Potentiometric Difference Titration," *Biochemistry*, 19:6129–6137 (1980).

Worku et al., "Identification of Histidyl and Cysteinyl Residues Essential for Catalysis by 5'–Nucleotidase," *FEBS Letters*, 167:235–240 (1984).

Smith et al., "Chemical Modification of Active Site Residues in γ–Glutamyl Transpeptidase," *The Journal of Biological Chemistry*, 270:12476–12480 (1995).

Smith et al., "Nonessentiality of the Active Sulfhydryl Group of Rabbit Muscle Creatine Kinase," *The Journal of Biological Chemistry*, 249:3317–3318 (1974).

Roberts et al., "Reactivity of Small Thiolate Anions and Cysteine–25 in Papain Toward Methyl Methanethiosulfonate," *Biochemistry*, 25:5595–5601 (1986).

Pardo et al., "Cysteine 532 and Cysteine 545 Are the N–Ethylmaleimide–Reactive Residues of the Neurospora Plasma Membrane $H^+$–ATPase," *The Journal of Biological Chemistry*, 264:9373–9379 (1989).

Hempel et al., "Selective Chemical Modification of Human Liver Aldehyde Dehydrogenases $E_1$ and $E_2$ by Iodoacetamide," *The Journal of Biological Chemistry*, 256:10889–10896 (1981).

Daly et al., "Formation of Mixed Disulfide Adducts at Cysteine–281 of the Lactose Repressor Protein Affects Operator And Inducer Binding Parameters," *Biochemistry*, 25:5468–5474 (1986).

Bodwell et al., "Sulfhydryl–Modifying Reagents Reversibly Inhibit Binding of Glucocorticoid–Receptor Complexes to DNA–Cellulose," *Biochemistry*, 23:1392–1398 (1984).

Alvear et al., "Inactivation of Chicken Liver Mevalonate 5–Diphosphate Decarboxylase by Sulfhydryl–Directed Reagents: Evidence of a Functional Dithiol," *Biochimica et Biophysica Acta*, 994:7–11 (1989).

Miller et al., "Peroxide Modification of Monoalkylated Glutathione Reductase," *The Journal of Biological Chemistry*, 266:19342–19350 (1991).

Soper et al., "Effects of Substrates on the Selective Modification of the Cysteinyl Residues of D–Amino Acid Transaminase," *The Journal of Biological Chemistry*, 254:10901–10905 (1979).

Stauffer et al., "Electrostatic Potential of the Acetylcholine Binding Sites in the Nicotinic Receptor Probed by Reactions Of Binding–Site Cysteines with Charged Methanethiosulfonates," *Biochemistry*, 33:6840–6849 (1994).

Nakayama et al., "Chemical Modification of Cysteinyl, Lysyl and Histidyl Residues of Mouse Liver 17β–Hydroxysteroid Dehydrogenase," *Biochimica et Biophysica Acta*, 1120:144–150 (1992).

Huang et al., "Improving the Activity of Immobilized Subtilisin by Site–Specific Attachment to Surfaces," *Anal. Chem.*, 69:4601–4607 (1997).

Brocklehurst, "Specific Covalent Modification of Thiols: Applications in the Study of Enzymes and Other Biomolecules," *Int. J. Biochem.*, 10:259–274 (1979).

Bruice et al., "Novel Alkyl Alkanethiolsulfonate Sulfhydryl Reagents. Modification of Derivatives of L–Cysteine," *Journal of Protein Chemistry*, 1:47–58 (1982).

Smith et al., "Simple Alkanethiol Groups for Temporary Blocking of Sulfhydryl Groups of Enzymes," *Biochemistry*, 14:766–771 (1975).

Polgar, "Spectrophotometric Determination of Mercaptide Ion, an Activated Form of SH–Group in Thiol Enzymes," *FEBS Letters*, 38:187–190 (1974).

Konigsberg, "Reduction of Disulfide Bonds in Proteins with Dithiothreitol," *Methods in Enzymology*, 25:185–188 (1972).

Kenyon et al., "Novel Sulfhydryl Reagents," *Methods Enzymol.*, 47:407–430 (1977).

Kluger et al., "Amino Group Reactions of the Sulfhydryl Reagent Methyl Methanesulfonothioate. Inactivation of D–3–hydroxybutyrate Dehydrogenase and Reaction with Amines in Water," *Can. J. Biochem.*, 58:629–632 (1980).

Kaiser, "Catalytic Activity of Enzymes Altered at Their Active Sites," *Angew. Chem. Int. Ed. Engl.*, 27:913–922 (1988).

Betzel et al., "Crystal Structure of the Alkaline Proteinase Savinase™ from *Bacillus lentus* at 1·4 Å Resolution," *J. Mol. Biol.*, 223:427–445 (1992).

DeSantis et al., "Chemical Modifications at a Single Site Can Induce Significant Shifts in the pH Profiles of a Serine Protease," *J. Am. Chem. Soc.*, 120:8582–8586 (1998).

DeSantis et al., "Site–Directed Mutagenesis Combined with Chemical Modification as a Strategy for Altering the Specificity of the $S_1$ and $S_1'$ Pockets of Subtilisin *Bacillus lentus*," *Biochemistry*, 37:5968–5973 (1998).

Plettner et al., "A Combinatorial Approach to Chemical Modification of Subtilisin *Bacillus lentus*," *Bioorganic & Medicinal Chemistry Letters*, 8:2291–2296 (1998).

* cited by examiner

US 6,395,532 B1

SEQUENCE LISTING

<160> NUMBER OF SEQ ID NOS: 2

<210> SEQ ID NO 1
<211> LENGTH: 269
<212> TYPE: PRT
<213> ORGANISM: Bacillus lentus
<220> FEATURE:
<223> OTHER INFORMATION: Subtilisin SBL

<400> SEQUENCE: 1

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
             20                  25                  30

Thr Gly Ile Ser Thr His Pro Asp Leu Asn Ile Arg Gly Gly Ala Ser
         35                  40                  45

Phe Val Pro Gly Glu Pro Ser Thr Gln Asp Gly Asn Gly His Gly Thr
     50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 2
<211> LENGTH: 275
<212> TYPE: PRT
<213> ORGANISM: Bacillus amyloliquefaciens
<220> FEATURE:
<223> OTHER INFORMATION: Subtilisin BPN'

<400> SEQUENCE: 2

```
Ala Gln Ser Val Pro Tyr Gly Val Ser Gln Ile Lys Ala Pro Ala Leu
 1               5                  10                  15

His Ser Gln Gly Tyr Thr Gly Ser Asn Val Lys Val Ala Val Ile Asp
```

-continued

```
                     20                  25                  30
Ser Gly Ile Asp Ser Ser His Pro Asp Leu Lys Val Ala Gly Gly Ala
            35                  40                  45
Ser Met Val Pro Ser Glu Thr Asn Pro Phe Gln Asp Asn Asn Ser His
        50                  55                  60
Gly Thr His Val Ala Gly Thr Val Ala Ala Leu Asn Asn Ser Ile Gly
 65                  70                  75                  80
Val Leu Gly Val Ala Pro Ser Ala Ser Leu Tyr Ala Val Lys Val Leu
                 85                  90                  95
Gly Ala Asp Gly Ser Gly Gln Tyr Ser Trp Ile Ile Asn Gly Ile Glu
            100                 105                 110
Trp Ala Ile Ala Asn Asn Met Asp Val Ile Asn Met Ser Leu Gly Gly
        115                 120                 125
Pro Ser Gly Ser Ala Ala Leu Lys Ala Ala Val Asp Lys Ala Val Ala
        130                 135                 140
Ser Gly Val Val Val Ala Ala Ala Gly Asn Glu Gly Thr Ser Gly
145                 150                 155                 160
Ser Ser Ser Thr Val Gly Tyr Pro Gly Lys Tyr Pro Ser Val Ile Ala
            165                 170                 175
Val Gly Ala Val Asp Ser Ser Asn Gln Arg Ala Ser Phe Ser Ser Val
            180                 185                 190
Gly Pro Glu Leu Asp Val Met Ala Pro Gly Val Ser Ile Gln Ser Thr
        195                 200                 205
Leu Pro Gly Asn Lys Tyr Gly Ala Tyr Asn Gly Thr Ser Met Ala Ser
        210                 215                 220
Pro His Val Ala Gly Ala Ala Ala Leu Ile Leu Ser Lys His Pro Asn
225                 230                 235                 240
Trp Thr Asn Thr Gln Val Arg Ser Ser Leu Glu Asn Thr Thr Thr Lys
            245                 250                 255
Leu Gly Asp Ser Phe Tyr Tyr Gly Lys Gly Leu Ile Asn Val Gln Ala
            260                 265                 270
Ala Ala Gln
        275
```

MODIFIED ENZYMES AND THEIR USE FOR PEPTIDE SYNTHESIS

CROSS-REFERENCE TO RELATED APPLICATIONS

This application claims priority to U.S. Provisional Patent Application Ser. No. 60/072,351, filed Jan. 23, 1998, and U.S. Provisional Patent Application Ser. No. 60/072,265, filed Jan. 23, 1998, and which are hereby incorporated by reference.

FIELD OF THE INVENTION

The present invention relates to modified enzymes with one or more amino acid residues being replaced by cysteine residues which are modified by replacing thiol hydrogen in at least some of the cysteine residues with a thiol side chain to form a modified enzyme. The modified enzyme has high esterase and low amidase activity. The present invention also relates to the use of modified enzymes in peptide synthesis.

BACKGROUND OF THE INVENTION

Modifying enzyme properties by site-directed mutagenesis has been limited to natural amino acid replacements, although molecular biological strategies for overcoming this restriction have recently been derived (Cornish et al., *Angew. Chem.*, Int. Ed. Engl., 34:621–633 (1995)). However, the latter procedures are difficult to apply in most laboratories. In contrast, controlled chemical modification of enzymes offers broad potential for facile and flexible modification of enzyme structure, thereby opening up extensive possibilities for controlled tailoring of enzyme specificity.

Changing enzyme properties by chemical modification has been explored previously, with the first report being in 1966 by the groups of Bender (Polgar et al., *J. Am. Chem. Soc.*, 88:3153–3154 (1966)) and Koshland (Neet et al., *Proc. Natl. Acad. Sci. USA*, 56:1606–1611 (1966)), who created a thiolsubtilisin by chemical transformation ($CH_2OH \rightarrow CH_2SH$) of the active site serine residue of subtilisin BPN' to cysteine. Interest in chemically produced artificial enzymes, including some with synthetic potential, was renewed by Wu (Wu et al., *J. Am. Chem. Soc.*, 111:4514–4515 (1989); Bell et al., *Biochemistry*, 32:3754–3762 (1993)) and Peterson (Peterson et al., *Biochemistry*, 34:6616–6620 (1995)), and, more recently, Suckling (Suckling et al., *Bioorg. Med. Chem. Lett.*, 3:531–534 (1993)).

Enzymes are now widely accepted as useful catalysts in organic synthesis. However, natural, wild-type, enzymes can never hope to accept all structures of synthetic chemical interest, nor always be transformed stereospecifically into the desired enantiomerically pure materials needed for synthesis. This potential limitation on the synthetic applicabilities of enzymes has been recognized, and some progress has been made in altering their specificities in a controlled manner using the site-directed and random mutagenesis techniques of protein engineering. However, modifying enzyme properties by protein engineering is limited to making natural amino acid replacements, and molecular biological methods devised to overcome this restriction are not readily amenable to routine application or large scale synthesis. The generation of new specificities or activities obtained by chemical modification of enzymes has intrigued chemists for many years and continues to do so.

U.S. Pat. No. 5,208,158 to Bech et al. ("Bech") describes chemically modified detergent enzymes where one or more methionines have been mutated into cysteines. The cysteines are subsequently modified in order to confer upon the enzyme improved stability towards oxidative agents. The claimed chemical modification is the replacement of the thiol hydrogen with $C_{1-6}$ alkyl.

Although Bech has described altering the oxidative stability of an enzyme through mutagenesis and chemical modification, it would also be desirable to develop one or more enzymes with altered properties such as activity, nucleophile specificity, substrate specificity, stereoselectivity, thermal stability, pH activity profile, and surface binding properties for use in, for example, detergents or organic synthesis. In particular, enzymes, such as subtilisins, tailored for peptide synthesis would be desirable. Enzymes useful for peptide synthesis have high esterase and low amidase activities. Generally, subtilisins do not meet these requirements and the improvement of the esterase to amidase selectivities of subtilisins would be desirable. However, previous attempts to tailor enzymes for peptide synthesis by lowering amidase activity have generally resulted in dramatic decreases in both esterase and amidase activities. Previous strategies for lowering the amidase activity include the use of water-miscible organic solvents (Barbas et al., *J. Am. Chem. Soc.*, 110:5162–5166 (1988); Wong et al., *J. Am. Chem. Soc.*, 112:945–953 (1990); and Sears et al., *Biotechnol. Prog.*, 12:423–433 (1996)) and site-directed mutagenesis (Abrahamsen et al., *Biochemistry*, 30:4151–4159 (1991); Bonneau et al., *J. Am. Chem. Soc.*, 113:1026–1030 (1991); and Graycar et al., *Ann. N. Y. Acad. Sci.*, 67:71–79 (1992)). However, while the ratios of esterase-to-amidase activities were improved by these approaches, the absolute esterase activities were lowered concomitantly. Abrahamsen et al., *Biochemistry*, 30:4151–4159 (1991). Chemical modification techniques (Neet et al., *Proc. Nat. Acad. Sci.*, 56:1606 (1966); Polgar et al., *J. Am. Chem. Soc.*, 88:3153–3154 (1966); Wu et al., *J. Am. Chem. Soc.*, 111:4514–4515 (1989); and West et al., *J. Am. Chem. Soc.*, 112:5313–5320 (1990)), which permit the incorporation of unnatural amino acid moieties, have also been applied to improve esterase to amidase selectivity of subtilisins. For example, chemical conversion of the catalytic triad serine (Ser221) of subtilisin to cysteine (Neet et al., *Proc. Nat. Acad. Sci.*, 56:1606 (1966); Polgar et al., *J. Am. Chem. Soc.*, 88:3153–3154 (1966); and Nakatsuka et al., *J. Am. Chem. Soc.*, 109:3808–3810 (1987)) or to selenocysteine (Wu et al., *J. Am. Chem. Soc.*, 111:4514–4515 (1989)), and methylation of the catalytic triad histidine (His57) of chymotrypsin (West et al., *J. Am. Chem. Soc.*, 112:5313–5320 (1990)), effected substantial improvement in esterase-to-amidase selectivities. Unfortunately however, these modifications were again accompanied by 50- to 1000-fold decreases in absolute esterase activity.

The present invention is directed to overcoming these deficiencies.

SUMMARY OF THE INVENTION

One aspect of the present invention relates to modified enzymes with one or more amino acid residues from an enzyme being replaced by cysteine residues, where at least some of the cysteine residues are modified by replacing thiol hydrogen in the cysteine residue with a thiol side chain to form a modified enzyme, where the modified enzyme has high esterase and low amidase activity.

Another aspect of the present invention relates to a method of producing a modified enzyme. This method involves providing an enzyme with one or more amino acids in the enzyme being replaced with cysteine residues and replacing thiol hydrogen in at least some of the cysteine residues with a thiol side chain to form a modified enzyme. The modified enzyme has high esterase and low amidase activity.

The present invention also relates to a method of peptide synthesis. This method includes providing a modified enzyme with one or more amino acid residues in the enzyme being replaced by cysteine residues, where at least some of the cysteine residues are modified by replacing thiol hydrogen in the cysteine residue with a thiol side chain, where the modified enzyme exhibits high esterase and low amidase activity. An acyl donor, an acyl acceptor, and the modified enzyme are then combined under conditions effective to form a peptide product.

The modified enzymes of the present invention provide an alternative to site-directed mutagenesis and chemical modification for introducing unnatural amino acids into proteins. In addition, these modified enzymes more efficiently catalyze peptide synthesis as a result of an increased esterase-to-amidase ratio compared to wild-type enzymes. Further, the modified enzymes of the present invention can incorporate D-amino acid esters as acyl donors in peptide synthesis and α-branched amides as acyl acceptors in peptide synthesis to form a variety of dipeptides which cannot be produced with wild-type ("WT") enzymes.

DETAILED DESCRIPTION OF THE INVENTION

The present invention relates to modified enzymes with one or more amino acid residues from an enzyme being replaced by cysteine residues, where at least some of the cysteine residues are modified by replacing thiol hydrogen in the cysteine residue with a thiol side chain to form a modified enzyme. The modified enzyme has high esterase and low amidase activity.

Figure 1:
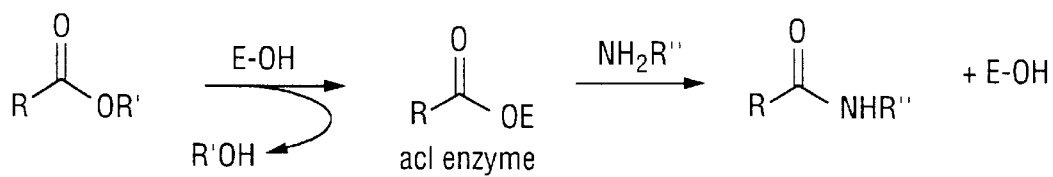
FIG. 1 shows peptide coupling catalyzed by an enzyme.

Preferably, the enzyme is a protease. More preferably, the enzyme is a Bacillus subtilisin. Subtilisins are alkaline serine proteases that are finding increasing use in biocatalysis, particularly in chiral resolution, regioselective acylation of polyfunctional compounds, peptide coupling, and glycopeptide synthesis. The latter two applications are of particular interest, because they provide an alternative to site-directed mutagenesis and chemical modification for introducing unnatural amino acids into proteins. As shown in FIG. 1, subtilisins can catalyze peptide bond formation starting from an ester substrate, by first forming an acyl enzyme intermediate which then reacts with a primary amine to form the peptide product. This application thus requires high esterase activity to promote acyl enzyme formation and then low amidase activity to minimize hydrolysis of the peptide bond of the desired product. Generally, subtilisins do not meet these requirements and the improvement of the esterase to amidase selectivities of subtilisins has been a long sought after goal.

Also, preferably, the amino acids replaced in the enzyme by cysteines are selected from the group consisting of asparagine, leucine, methionine, or serine. More preferably, the amino acid to be replaced is located in a subsite of the enzyme, preferably, the $S_1$, $S_1$', or $S_2$ subsites. Most preferably, the amino acids to be replaced are N62, L217, M222, and S166 where the numbered position corresponds to naturally-occurring subtilisin from *Bacillus amyloliquefaciens* or to equivalent amino acid residues in other subtilisins, such as *Bacillus lentus* subtilisin.

In a particularly preferred embodiment, the enzyme is a *Bacillus lentus* subtilisin. In another particularly preferred embodiment, the amino acid to be replaced by cysteine is N62, L217, S 166, or M222 and the thiol side chain group is selected from the group consisting of:

—$SCH_3$;
—$SCH_2CH_3$;
—$SCH_2CH(CH_3)_2$;
—$S(CH_2)_4CH_3$;
—$S(CH_2)_5CH_3$;
—$S(CH_2)_9CH_3$;
—$SCH_2C_6H_5$;
—$SCH_2CH_2NH_3^+$; and
—$SCH_2CH_2SO_3^-$; or the amino acid to be replaced by cysteine is S166 or M222 and the thiol side chain group is selected from the group consisting of:

—$SCH_2C_6H_5$;
—$SCH_2P$-$COOH$-$C_6H_4$);
—$SCH_2C_6F_5$; and
—$SCH_2CH_2NH_3^+$.

Preferably, the modified enzymes of the present invention have an esterase activity of from about 3.5 $s^{-1}$ $mM^{-1}$ to about 1110000 $s^{-1}$ $mM^{-1}$ and an amidase activity of from about 0.056 $s^{-1}$ $mM^-$to about 35500 $s^{-1}$ $mM^{-1}$. Most preferably, the modified enzymes of the present invention have an esterase activity from about 350 $s^{-1}$ $mM^{-1}$ to about 11100 $s^{-1}$ $mM^{-1}$ and an amidase activity of from about 5.6 $s^{-1}$ $mM^{-1}$ to about 355 $s^{-1}$ $mM^{-1}$.

A "modified enzyme" is an enzyme that has been changed by replacing an amino acid residue such as asparagine, serine, methionine, or leucine with a cysteine residue and then replacing the thiol hydrogen of at least some of the cysteine with a thiol side chain (e.g., $-SCH_3$, $-SCH_2CH_3$, $-SCH_2CH(CH_3)_2$, $-S(CH_2)_4CH_3$, $-S(CH_2)_5CH_3$, $-S(CH_2)_9CH_3$, $-SCH_2C_6H_5$, $-SCH_2CH_2NH_3^+$, $-SCH_2CH_2SO_3^-$, $-SCH_2(P\text{-}COOH-C_6H_4)$, and $-SCH_2C_6F_5$). After modification, the properties of the enzyme, i.e., activity or substrate specificity, may be altered. Preferably, the activity of the enzyme is increased.

The term "enzyme" includes proteins that are capable of catalyzing chemical changes in other substances without being changed themselves. The enzymes can be wild-type enzymes or variant enzymes. Enzymes within the scope of the present invention include pullulanases, proteases, cellulases, amylases, isomerases, lipases, oxidases, and reductases. The enzyme can be a wild-type or mutant protease. Wild-type proteases can be isolated from, for example, *Bacillus lentus* or *Bacillus amyloliquefaciens* (also referred to as BPN'). Mutant proteases can be made according to the teachings of, for example, PCT Publication Nos. WO 95/10615 and WO 91/06637, which are hereby incorporated by reference.

Several types of moieties can be used to replace the thiol hydrogen of the cysteine residue. These include $-SCH_3$, $-SCH_2CH_3$, $-SCH_2CH(CH_3)_2$, $-S(CH_2)_4CH_3$, $-S(CH_2)_5CH_3$, $-S(CH_2)_9CH_3$; $-SCH_2C_6H_5$, $-SCH_2CH_2NH_3^+$, $-SCH_2CH_2SO_3^-$, $-SCH_2(p\text{-}COOH-C_6H_4)$, and $-SCH_2C_6F_5$.

The terms "thiol side chain group," "thiol containing group," and "thiol side chain" are terms which are can be used interchangeably and include groups that are used to replace the thiol hydrogen of a cysteine used to replace one of the amino acids in an enzyme. Commonly, the thiol side chain group includes a sulfur through which the thiol side chain groups defined above are attached to the thiol sulfur of the cysteine.

The binding site of an enzyme consists of a series of subsites across the surface of the enzyme. The substrate residues that correspond to the subsites are labeled P and the subsites are labeled S. By convention, the subsites are labeled $S_1$, $S_2$, $S_3$, $S_4$, $S_1'$, and $S_2'$. A discussion of subsites can be found in Siezen et al., *Protein Engineering*, 4:719–737 (1991) and Fersht, *Enzyme Structure and Mechanism*, 2 ed., Freeman: N.Y., 29–30 (1985), which are hereby incorporated by reference. The preferred subsites are $S_1$, $S_1'$, and $S_2$.

Another aspect of the present invention relates to a method of producing a modified enzyme. This method involves providing an enzyme with one or more amino acids in the enzyme being replaced with cysteine residues and replacing thiol hydrogen in at least some of the cysteine residues with a thiol side chain to form a modified enzyme. The modified enzyme has high esterase and low amidase activity.

The amino acid residues of the present invention can be replaced with cysteine residues using site-directed mutagenesis methods or other methods well known in the art. See, for example, PCT Publication No. WO 95/10615, which is hereby incorporated by reference. One method of modifying the thiol hydrogen of the cysteine residue is set forth in the Examples.

The present invention also relates to a method of peptide synthesis. This method includes providing a modified enzyme with one or more amino acid residues in the enzyme being replaced by cysteine residues, where at least some of the cysteine residues are modified by replacing thiol hydrogen in the cysteine residue with a thiol side chain, where the modified enzyme exhibits high esterase and low amidase activity. An acyl donor, an acyl acceptor, and the modified enzyme are combined under conditions effective to form a peptide product.

Enzymatic peptide coupling is an attractive method for preparation of a variety of peptides, because this method requires minimal protection of the substrate, proceeds under mild conditions, and does not cause racemization. Wong et al., *Enzymes in Synthetic Organic Chemistry*, Pergamon Press: Oxford, 41–130 (1994), which is hereby incorporated by reference. In spite of these advantages, two major problems have limited the use of serine proteases in peptide synthesis. One is their efficient proteolytic (amidase) activity which causes hydrolysis of the coupling product, and the other is their stringent structural specificity and stereospecificity.

The modified enzymes of the present invention have altered esterase-to-amidase activity as compared to the precursor enzyme. Increasing the esterase-to-amidase ratio enables the use of the enzyme to more efficiently catalyze peptide synthesis. In particular, subtilisins can catalyze peptide bond formation starting from an ester substrate (i.e. an acyl donor), by first forming an acyl enzyme intermediate which then reacts with a primary amine (i.e. an acyl acceptor) to form the peptide product, as shown in FIG. 1. This reaction thus requires high esterase activity to promote acyl enzyme formation and, then, low amidase activity to minimize hydrolysis of the peptide bond of the desired product. Modified enzymes of the present invention show an increased esterase-to-amidase ratio, without reducing the absolute esterase activity of the enzyme. In addition, certain modified enzymes of the present invention even show a concomitant increase in the absolute esterase activity.

Further, the modified enzymes of the present invention present a significant enlargement of the applicability of chemically modified mutants of subtilisin *Bacillus lentus* in peptide synthesis. The chemically modified mutant enzymes of the present invention can incorporate D-amino acid esters as acyl donors in peptide synthesis or an (α-branched amino acid amide as acyl acceptor in peptide synthesis to give a variety of dipeptides. These reactions are not possible with subtilisin *Bacillus lentus*-wild type (WT).

Therefore, the modified enzymes of the present invention can be used in organic synthesis to, for example, catalyze a desired reaction and/or favor a certain stereoselectivity. See e.g., Noritomi et al. *Biotech. Bioeng.* 51:95–99 (1996); Dabulis et al. *Biotech. Bioeng.* 41:566–571 (1993), and Fitzpatrick et al. *J. Am. Chem. Soc.* 113:3166–3171 (1991), which are hereby incorporated by reference.

The modified enzymes of the present invention can be formulated into known powdered and liquid detergents having a pH between 6.5 and 12.0 at levels of about 0.01 to about 5% (preferably 0.1% to 0.5%) by weight. These detergent cleaning compositions or additives can also include other enzymes, such as known proteases, amylases, cellulases, lipases, or endoglycosidases, as well as builders and stabilizers.

The modified enzymes of the present invention, especially subtilisins, are useful in formulating various detergent compositions. A number of known compounds are suitable surfactants useful in compositions comprising the modified enzymes of the present invention. These include nonionic, anionic, cationic, anionic, or zwitterionic detergents, as disclosed in U.S. Pat. No. 4,404,128 to Anderson and U.S. Pat. No. 4,261,868 to Flora et al., which are hereby incorporated by reference. A suitable detergent formulation is that described in Example 7 of U.S. Pat. No. 5,204,015 to Caldwell et al., which is hereby incorporated by reference. The art is familiar with the different formulations which can be used as cleaning compositions. In addition to typical cleaning compositions, it is readily understood that the modified enzymes of the present invention may be used for any purpose that native or wild-type enzymes are used. Thus, these modified enzymes can be used, for example, in bar or liquid soap applications, dishcare formulations, contact lens cleaning solutions or products, peptide synthesis, feed applications such as feed additives or preparation of feed additives, waste treatment, textile applications such as the treatment of fabrics, and as fusion-cleavage enzymes in protein production. The modified enzymes of the present invention may achieve improved wash performance in a detergent composition (as compared to the precursor). As used herein, improved wash performance in a detergent is defined as increasing cleaning of certain enzyme-sensitive stains such as grass or blood, as determined by light reflectance evaluation after a standard wash cycle.

The addition of the modified enzymes of the present invention to conventional cleaning compositions does not create any special use limitation. In other words, any temperature and pH suitable for the detergent is also suitable for the present compositions as long as the pH is within the above range and the temperature is below the described modified enzyme's denaturing temperature. In addition, modified enzymes in accordance with the invention can be used in a cleaning composition without detergents, again either alone or in combination with builders and stabilizers.

In another aspect of the present invention, the modified enzymes are used in the preparation of an animal feed, for example, a cereal-based feed. The cereal can be at least one of wheat, barley, maize, sorghum, rye, oats, triticale, and rice. Although the cereal component of a cereal-based feed constitutes a source of protein, it is usually necessary to include sources of supplementary protein in the feed such as those derived from fish-meal, meat-meat, or vegetables. Sources of vegetable proteins include at least one of full fat soybeans, rapeseeds, canola, soybean-meal, rapeseed-meal, and canola-meal.

The inclusion of a modified enzyme of the present invention in an animal feed can enable the crude protein value and/or digestibility and/or amino acid content and/or digestibility coefficients of the feed to be increased, which permits a reduction in the amounts of alternative protein sources and/or amino acids supplements which had previously been necessary ingredients of animal feeds.

The feed provided by the present invention may also include other enzyme supplements such as one or more of β-glucanase, glucoamylase, mannanase, α-galactosidase, phytase, lipase, α-arabinofuranosidase, xylanase, α-amylase, esterase, oxidase, oxido-reductase, and pectinase. It is particularly preferred to include a xylanase as a further enzyme supplement such as a subtilisin derived from the genus Bacillus. Such xylanases are, for example, described in detail in PCT Patent Application No. WO 97/20920, which is hereby incorporated by reference.

Another aspect of the present invention is a method for treating a textile. The method includes providing a modified enzyme with one or more amino acid residues from an enzyme being replaced by cysteine residues, wherein the cysteine residues are modified by replacing thiol hydrogen in at least some of the cysteine residues with a thiol side chain to form a modified enzyme, where the modified enzyme has high esterase and low amidase activity. The modified enzyme is contacted with a textile under conditions effective to produce a textile resistance to certain enzyme-sensitive stains. Such enzyme-sensitive stains include grass and blood. Preferably, the textile includes a mutant enzyme. The method can be used to treat, for example, silk or wool as described in publications such as Research Disclosure 216,034, European Patent Application No. 134,267, U.S. Pat. No. 4,533,359, and European Patent Application No. 344,259, which are hereby incorporated by reference.

EXAMPLES

Example 1

Producing the Cys-Mutants

The gene for subtilisin from *Bacillus lentus* ("SBL") was cloned into the bacteriophage M13mp19 vector for mutagenesis (U.S. Pat. No. 5,185,258, which is hereby incorporated by reference). Oligonucleotide-directed mutagenesis was performed as described in Zoller et al., *Methods Enzymol.*, 100:468–500 (1983), which is hereby incorporated by reference. The mutated sequence was cloned, excised, and reintroduced into the expression plasmid GG274 in the *B. subtilis* host. PEG (50%) was added as a stabilizer. The crude protein concentrate obtained was purified by first passing through a Sephadex™ G-25 desalting matrix with a pH 5.2 buffer (20 mM sodium acetate, 5 mM $CaCl_2$) to remove small molecular weight contaminants. Pooled fractions for the desalting column were then applied to a strong cation exchange column (SP Sepharose™ FF) in the sodium acetate buffer (above), and SBL was eluted with a one step gradient of 0–200 mM NaCl acetate buffer, pH 5.2. Salt-free enzyme powder was obtained following dialysis of the eluent against Millipore purified water, and subsequent lyophilization. The purity of the mutant and wild-type enzymes, which had been denatured by incubation with 0.1 M HCl at 0° C. for 30 minutes, was ascertained by SDS-PAGE on homogeneous gels using the Phast™ System from Pharmacia (Uppsala, Sweden). The concentration of SBL was determined using the Bio-Rad (Hercules, Calif.) dye reagent kit which is based on the method of Bradford, *Analytical Biochemistry*, 72:248–254 (1976), which is hereby incorporated by reference. Specific activity of the enzymes was determined in pH 8.6 buffer using the method described in Example 3 below.

Example 2

Preparation of Certain Moieties

Preparation of 2, 3, 4, 5, 6-pentafluorobenzyl methanethiosulfonate 2, 3, 4, 5, 6-pentafluorobenzyl methanethiosulfonate was prepared according to the general procedure in Examples 1 and 3 from α-bromo-2,3,4,5,6-pentafluorotoluene in 88% yield. m.p.: 64.2–64.7° C. (95% EtOH); IR (KBr): 3030, 3009, 2961, 2930, 2920, 1514, 1314, 1132, 980, 880, and 748 $cm^{-1}$; $^1$H NMR (200 MHz, $CDCl_3$): δ4.46 (br s, 2H, $SCH_2$), 3.36 (s, 3H, $CH_3SO_2$); MS (EI): 292 ($M^+$), 212 ($^+S=CHC_6F_5$); HRMS (EI): 291.9648 ($M^+$, calc'd for $C_8H_5F_5O_2S_2$: 291.9651).

Preparation of 4-carboxybenzyl methanethiosulfonate

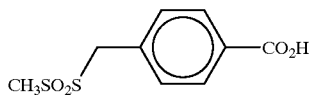

4-carboxybenzyl methanethiosulfonate was prepared according to the general procedure in Examples 1 and 3 from α-bromo-β-toluic acid in 60% yield after recrystallization from 95% EtOH. m.p.:187.6–187.8° C.; IR (KBr): 3300–2200, 1683, 1608, 1577, 1422, 1301, 1180, 1121, 957, 863, 750, 716, and 551 cm$^{-1}$; $^1$H NMR (200 MHz, DMSO-d$_6$ and 10% D$_2$O): δ7.90 (d, J=8.0 Hz, 2H, aromatic), 7.51 (d, J=8.0 Hz, 2H, aromatic), 4.47 (s, 2H, SCH$_2$), 3.23 (3H, CH$_3$SO$_2$S); $^{13}$C NMR (50 MHz, DMSO-d$_6$ and 10% D$_2$O): δ167.87, 141.55, 130.56, 130.45, 130.07, 51.01, 39.37; MS (EI): 246 (M$^+$), 229 (M$^+$)—OH), 166 (base peak, $^+$S=CH—Ar); HRMS (EI): 246.0031 (M$^+$, calc'd. for C$_9$H$_{10}$O$_4$S$_2$: 246.0021).

Example 3

Peptide Synthesis Using Modified Enzymes with Alkyl Moieties

Materials

Succinyl-alanine-alanine-proline-phenylalanine-para-nitroanalide ("suc-AAPF-pNA") and succinyl-alanine-alanine-proline-phenylalanine-thiobenzyl ester ("suc-AAPF-SBn") were both from Bachem Inc. (Torrance, Calif.), Ellman's reagent (5,5'-dithiobis-2,2'-nitrobenzoic acid, DTNB) and phenylmethanesulfonyl fluoride ("PMSF") were from Sigma-Aldrich Inc. (Milwaukee, Wis.). Sources and syntheses of methanethiosulfonate ("MTS") reagents were as described in Berglund et al., *J. Am. Chem. Soc.*, 119:5265–5266 (1997), which is hereby incorporated by reference. Buffers, 2-[N-cyclohexylamino] ethanesulfonic acid (CHES), 4-morpholineethanesulfonic acid (MES) and tris hydroxymethylaminomethane (Tris) were from Sigma-Aldrich Inc. (Milwaukee, Wis.). Wild type SBL and cysteine mutants N62C, S166C, L217C, and M222C were provided by Genencor International Inc., Rochester, N.Y. and purified as described in Example 1 and Stabile et al., *Bioorg. Med. Chem. Lett.*, 6:2501–2506 (1996), which is hereby incorporated by reference.

Chemical Modification

Chemical modification with alkyl MTS reagents was carried out as described in Berglund et al., *J. Am. Chem. Soc.*, 119:5265–5266 (1997) and DeSantis et al., *Biochemistry*, 37:5968–5973 (1998), which are hereby incorporated by reference. Briefly, 200 μL of a 1 M solution of MTS reagent in a suitable solvent was added to a solution (5–10 mg/mL, 3.5 mL) of the cysteine mutant in 70 mM CHES, 5 mM MES, 2 mM CaCl$_2$ pH 9.5. The MTS reagent was added in two portions over 30 minutes. Reaction mixtures were kept at 20° C. with continuous end-over-end mixing. Reactions were monitored by following the specific activity with suc-AAPF-pNA and by tests for residual free thiol with Ellman's reagent. Once the reaction was complete, the reaction mixture was loaded on a Sephadex PD-10 G25 column with 5 mM MES and 2 mM CaCl$_2$, pH 6.5. The protein fraction was dialyzed against 1 mM CaCl$_2$, and the dialysate was lyophilized.

Characterization of Modified Enzymes

The molecular mass of each modified enzyme ("ME") was determined by electrospray ionization mass spectrometry (Berglund et al., *J. Am. Chem. Soc.*, 119:5265–5266 (1997); DeSantis et al., *Biochemistry*, 37:5968–5973 (1998), which are hereby incorporated by reference). The purity of the MEs was ascertained by native PAGE on 8–25% gels using the Phast system from Pharmacia (Uppsala, Sweden). The extent of chemical modification of the cysteine mutants was determined by thiol titration with DTNB for the 62, 217 and 166 mutants and with I$_2$ (Cunningham et al., *J. Biol. Chem.*, 234:1447–1451 (1959), which is hereby incorporated by reference) for the more sterically hindered 222 mutants which do not react with DTNB. Active site titrations were performed on all enzymes by monitoring the burst of fluoride released upon addition of phenylmethanesulfonyl fluoride to the enzyme, as described in Hsia et al., *J. Anal. Biochem.*, 242:221–227 (1996), which is hereby incorporated by reference.

Rapid Screen on Microtiter Plates

Detailed procedures and validation of this assay have been described in Plettner et al., *Bioorg. Med. Chem. Lett.*, 8:2291–2296 (1998), which is hereby incorporated by reference. Briefly, enzyme solutions were prepared in 5 mM MES with 2 mM CaCl$_2$, pH 6.5 at about 10$^{-7}$ M for amidase and 10$^{-8}$ M for esterase. Substrate solutions in DMSO were 1.6 mM (amidase) and 1.0 mM (esterase). The assay was performed at pH 8.6 in the same buffer used for kinetics (see below). Enzyme solutions were arranged on a microtiter plate (loading plate) along columns, with the last well in each column as a buffer blank. On a separate plate (assay plate), 10 μL of substrate and 180 μL of buffer was added to each well. Reactions were initiated by transferring 10 μL of enzyme from an appropriate column on the loading plate to the assay plate. Reactions were monitored on a Multiscan MCC 340 96-well reader programmed in the kinetic mode at 414 nm, with no time lag, at 5 second intervals for a total time of 1 minute (amidase) and 30 seconds (esterase). Background hydrolysis was subtracted automatically. The k$_{cat}$/K$_M$ was estimated from the rate of substrate hydrolysis (v) using the low-substrate approximation: v≈k$_{cat}$/K$_M$[E][S] where, [S]<<K$_M$.

Kinetics

Assays were done in 0.1 M Tris pH 8.6 containing 0.005% Tween. Substrate solutions were prepared in DMSO. In the esterase assay, substrate solutions also contained 0.0375 M DTNB (Bonneau et al., *J. Am. Chem. Soc.*, 113:1026–1030 (1991), which is hereby incorporated by reference). Concentrations of substrate stock solutions ranged from 0.013 to 0.3 M for amidase and 0.0015 to 0.3 M for esterase, and 9–10 different concentrations were tested in duplicate for each enzyme. Enzyme solutions were prepared in 20 mM MES, 1 mM CaCl$_2$, pH 5.8, at a concentration of 10$^{-6}$ M for amidase and 10$^{-7}$ M for esterase. Reactions were monitored spectrophotometrically on a Perkin Elmer Lambda 2 instrument equipped with a thermostatted cell compartment.

Prior to an assay, 980 μL of Tris buffer in a cuvette was equilibrated to 25° C. Substrate stock solution (10 μL) was added to the buffer and the reading set to zero. Reactions were initiated by addition of 10 μL of enzyme solution and were monitored at 410 nm (amidase) and 412 nm (esterase). Extinction coefficients for the chromophores were 8800 M$^{-1}$ cm$^{-1}$ for p-nitroaniline (Bonneau et al., *J. Am. Chem. Soc.*, 113:1026–1030 (1991), which is hereby incorporated by reference) and 13470 M$^{-1}$ cm$^{-1}$ for 3-carboxylate-4-nitrothiophenolate in 0.1 M Tris pH 8.6 with 0.005% Tween. Initial rates were obtained by linear fitting up to 5% conversion; r values exceeded 0.9996. In the case of esterase, rates in the presence of enzyme were corrected for uncatalyzed background hydrolysis of the thiobenzyl ester. Kinetic constants were obtained by fitting the rate data to the Michaelis-Menten equation using Grafit.® (Erithacus Software Ltd., Staines, Middlesex, United Kingdom)

Reaction of the Cysteine Mutants with DTNB

Since [DTNB]>>[enzyme] and [DTNB]≈constant over 30 seconds (time for 5% conversion), the pseudo-first order rate constant for the reaction of N62C, L217C and S166C mutants with DTNB was determined under the same conditions as used in the assay, using enzyme concentrations from $10^{-6}$ to $10^{-4}$ M. The pseudo first-order rates constant of reaction of N62C, L217C, and S166C with DTNB under the esterase assay conditions were $1.8 \times 10^{-4}$ $s^{-1}$ (0.5%= maximum amount of cysteine mutant reacted with DTNB over the time of the esterase assay), $1.4 \times 10^{-3}$ $S^{-1}$ (4.2% reacted), and $1.4 \times 10^{-4}$ $s^{-1}$ (0.4% reacted), respectively. The M222C mutant did not detectably react with DTNB.

Results

Each of the N62C, L217C, S166C, and M222C mutants of SBL were prepared and purified, and the introduced —$CH_2SH$ side-chain specifically and quantitatively chemically modified with the MTS reagents with alkyl moieties —$SCH_3$, —$SCH_2CH_3$, —$SCH_2CH(CH_3)_2$, —$S(CH_2)_4CH_3$, —$S(CH_2)_5CH_3$, —$S(CH_2)_9CH_3$, —$SCH_2C_6H_5$, —$SCH_2CH_2NH_3^+$, —$SCH_2CH_2SO_3^-$ (-a-i), as described previously (Berglund et al., *Bioorg. Med. Chem. Lett.*, 6:2507–2512 (1996); Berglund et al., *J. Am. Chem. Soc.*, 119:5265–5266 (1997); DeSantis et al., *Biochemistry*, 37:5968–5973 (1998); and DeSantis et al., *J. Am. Chem. Soc.*, 120:8582–8586 (1998), which are hereby incorporated by reference). The purities of the MEs generated were established by native polyacrylamide gel electrophoresis (PAGE), which showed only one band in each case, thereby demonstrating that the MEs were pure and that dimerization had not occurred. Mass analyses of the MEs by electrospray mass spectrometry were consistent (±6 Da) with the calculated masses for single-site modifications. Berglund et al., *J. Am. Chem. Soc.*, 119:5265–5266 (1997) and DeSantis et al., *Biochemistry*, 37:5968–5973 (1998). Titration of the N62C, S166C, and L217C MEs with Ellman's reagent showed a residual thiol content of less than 2% in all cases, confirming that the MTS reactions were virtually quantitative. Ellman et al., *Biochem. Pharmacol.*, 7:88–95 (1961), which is hereby incorporated by reference. The residual free thiol content for the more sterically hindered M222C MEs, which did not react with Ellman's reagent, was determined with 12 (Cunningham et al., *J. Biol. Chem.*, 234:1447–1451 (1959)). The M222C MEs contained ≦2% free thiol, except for M222C—$SCH_2CH_2SO_3^-$ (-i) which contained 3% residual thiol groups. The concentration of active enzyme was determined by active site titration with phenylmethanesulfonyl fluoride (PMSF). Hsia et al., *J. Anal. Biochem.*, 242:221–227 (1996). All of the MEs were 60–80% active by weight, except for M222C—$SCH_2CH_2SO_3^-$ (-i) which contained only 4% active enzyme and was, therefore, not investigated further.

Figure 2:
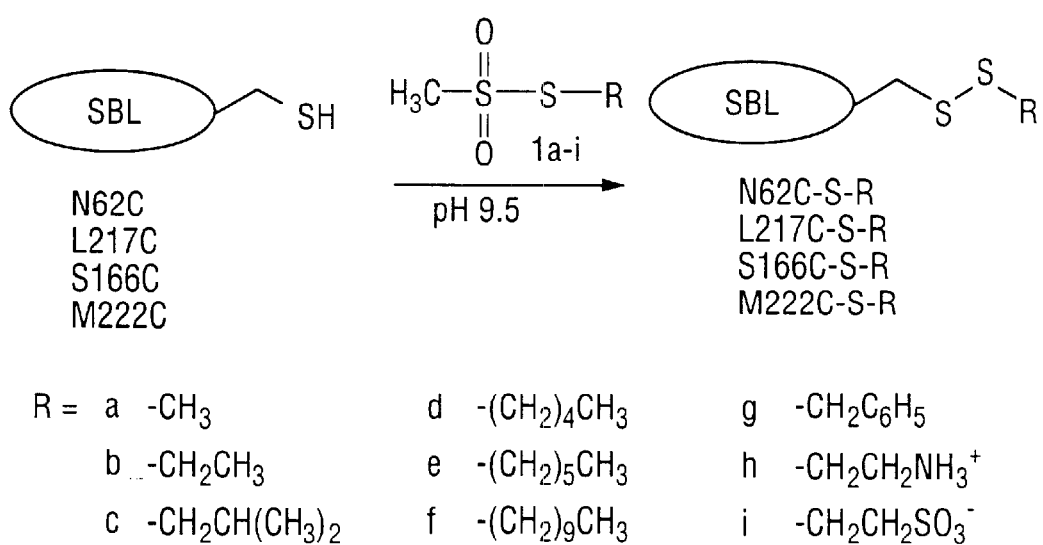
FIG. 2 shows the chemical modification of subtilisin *Bacillus lentus* mutants to generate chemically modified mutant enzymes.

Initially, a rapid screen on microtiter plates (Plettner et al., *Bioorg. Med. Chem. Lett.*, 8:2291–2296 (1998), which is hereby incorporated by reference) was used to generate estimates of $k_{cat}/K_M$ for amidase and esterase for the enzymes outlined in FIG. 2. Of 36 MEs and four cysteine mutants screened, 25 enzymes were chosen for further kinetic analyses. These included all the promising esterases, as well as a few mutants with severely damaged esterase activity for comparison. The results of the kinetic analyses with suc-AAPF-pNA and suc-AAPF-SBn as standard amide and ester substrates respectively, are presented in Table 1, below. It was recognized that the cysteine thiol of the unmodified cysteine mutants N62C, L217C, S166C, and M222C could react with DTNB, which is used in the kinetic assay to detect the thiol benzyl hydrolysis product of the esterase reaction. This possibility was discounted by studying the rates of reaction of DTNB with N62C, S 166C, L217C, and β-mercaptoethanol as a model for a non-hindered thiol which established that these did not react at a rate sufficient to interfere with the assay at the concentrations used.

TABLE 1

Kinetic constants of chemically modified mutants for amidase and esterase activities

| Enzyme | Amidase[a] | | | Esterase[b] | | |
|---|---|---|---|---|---|---|
| | $k_{cat}$ $(s^{-1})$[c] | $K_M$ (mM)[c] | $k_{cat}/K_M$ $(s^{-1}$ $mM^{-1})$ | $k_{cat}$ $(s^{-1})$[c] | $K_M$ (mM)[c] | $k_{cat}/K_M$ $(s^{-1}$ $mM^{-1})$ |
| WT | 153 ± 4 | 0.73 ± 0.05 | 209 ± 15 | 1940 ± 180 | 0.54 ± 0.07 | 3560 ± 540[d] |
| N62C | 163 ± 8 | 1.9 ± 0.2 | 86 ± 10 | 2370 ± 90 | 0.54 ± 0.06 | 4380 ± 510 |
| N62C-S-a | 73 ± 2 | 0.55 ± 0.04 | 133 ± 10 | 3130 ± 90 | 0.31 ± 0.03 | 10100 ± 1000 |
| N62C-S-b | 97 ± 2 | 0.55 ± 0.04 | 177 ± 13 | 2220 ± 110 | 0.2 ± 0.04 | 11100 ± 2300 |
| N62C-S-c | 139 ± 4 | 0.75 ± 0.06 | 185 ± 16 | 2180 ± 80 | 0.25 ± 0.04 | 8700 ± 1430 |
| N62C-S-e | 146 ± 7 | 0.63 ± 0.08 | 230 ± 30 | 2330 ± 150 | 0.26 ± 0.06 | 8970 ± 2150 |
| N62C-S-f | 124 ± 4 | 0.36 ± 0.04 | 344 ± 40 | 1000 ± 47 | 0.39 ± 0.06 | 2570 ± 410 |
| N62C-S-g | 121 ± 3 | 0.34 ± 0.03 | 355 ± 33 | 1840 ± 110 | 0.29 ± 0.06 | 6330 ± 1360 |
| N62C-S-h | 96 ± 5 | 1.0 ± 0.1 | 98 ± 11 | 2660 ± 80 | 0.48 ± 0.04 | 5540 ± 490 |
| N62C-S-i | 111 ± 4 | 0.93 ± 0.07 | 120 ± 10 | 3190 ± 110 | 0.61 ± 0.06 | 5230 ± 540 |
| L217C | 38 ± 1 | 0.80 ± 0.04 | 48 ± 3 | 3160 ± 120 | 0.57 ± 0.06 | 5540 ± 620 |
| L217C-S-a | 47 ± 2 | 0.62 ± 0.07 | 76 ± 9 | 2520 ± 120 | 0.56 ± 0.07 | 4500 ± 600 |
| L217C-S-c | 93 ± 2 | 0.61 ± 0.03 | 152 ± 8 | 2450 ± 70 | 0.31 ± 0.03 | 7900 ± 800 |
| L217C-S-d | 87 ± 3 | 0.52 ± 0.05 | 167 ± 17 | 2280 ± 80 | 0.39 ± 0.04 | 5840 ± 640 |
| L217C-S-f | 120 ± 3 | 0.54 ± 0.03 | 223 ± 13 | 1840 ± 100 | 0.50 ± 0.08 | 3690 ± 620 |
| L217C-S-h | 36 ± 1 | 0.64 ± 0.06 | 56 ± 6 | 3070 ± 90 | 0.41 ± 0.04 | 7490 ± 760 |
| L217C-S-i | 83 ± 6 | 1.8 ± 0.2 | 47 ± 6 | 5060 ± 130 | 1.0 ± 0.1 | 5060 ± 520 |
| S166C | 42 ± 1 | 0.50 ± 0.05 | 84 ± 9 | 600 ± 70 | 1.7 ± 0.4 | 350 ± 90 |
| S166C-S-a | 46 ± 2 | 0.34 ± 0.05 | 135 ± 20 | 2320 ± 50 | 0.38 ± 0.03 | 6100 ± 500 |
| S166C-S-g | 23 ± 0.5 | 1.2 ± 0.1 | 20 ± 1 | 1530 ± 110 | 0.31 ± 0.08 | 4900 ± 1300 |
| S166C-S-h | 50 ± 1 | 0.68 ± 0.04 | 74 ± 5 | 1350 ± 50 | 0.61 ± 0.07 | 2200 ± 270 |
| S166C-S-i | 25 ± 1 | 1.3 ± 0.1 | 19 ± 1 | 1950 ± 90 | 1.9 ± 0.2 | 1030 ± 120 |
| M222C | 61 ± 2 | 0.81 ± 0.07 | 75 ± 6 | 3080 ± 140 | 0.58 ± 0.07 | 5300 ± 680 |

TABLE 1-continued

Kinetic constants of chemically modified mutants for amidase and esterase activities

| | Amidase[a] | | | Esterase[b] | | |
|---|---|---|---|---|---|---|
| Enzyme | $k_{cat}$ ($s^{-1}$)[c] | $K_M$ (mM)[c] | $k_{cat}/K_M$ ($s^{-1}$ $mM^{-1}$) | $k_{cat}$ ($s^{-1}$)[c] | $K_M$ (mM)[c] | $k_{cat}/K_M$ ($s^{-1}$ $mM^{-1}$) |
| M222C-S-a | 56 ± 2 | 0.91 ± 0.07 | 62 ± 6 | 2090 ± 120 | 1.3 ± 0.2 | 1610 ± 270 |
| M222C-S-h | 5.0 ± 0.2 | 0.91 ± 0.08 | 5.6 ± 0.9 | 1970 ± 140 | 0.4 ± 0.1 | 4920 ± 1280 |

[a]substrate: suc-AAPF-pNA;
[b]substrate: sucAAPF-SBn;
[c]determined by the method of initial rates;
[d]mean standard three (esterase) experiments.

The broad applicability of the chemical modification approach for achieving the goal of improved esterase-to-amidase selectivity without reducing absolute esterase activity is evident from the Table 1 data since of 25 MEs and cysteine mutants evaluated, fully 19 displayed improved esterase to amidase selectivity. Furthermore, 20 displayed esterase activity that was higher than WT (See FIG. 3).

Figure 3:
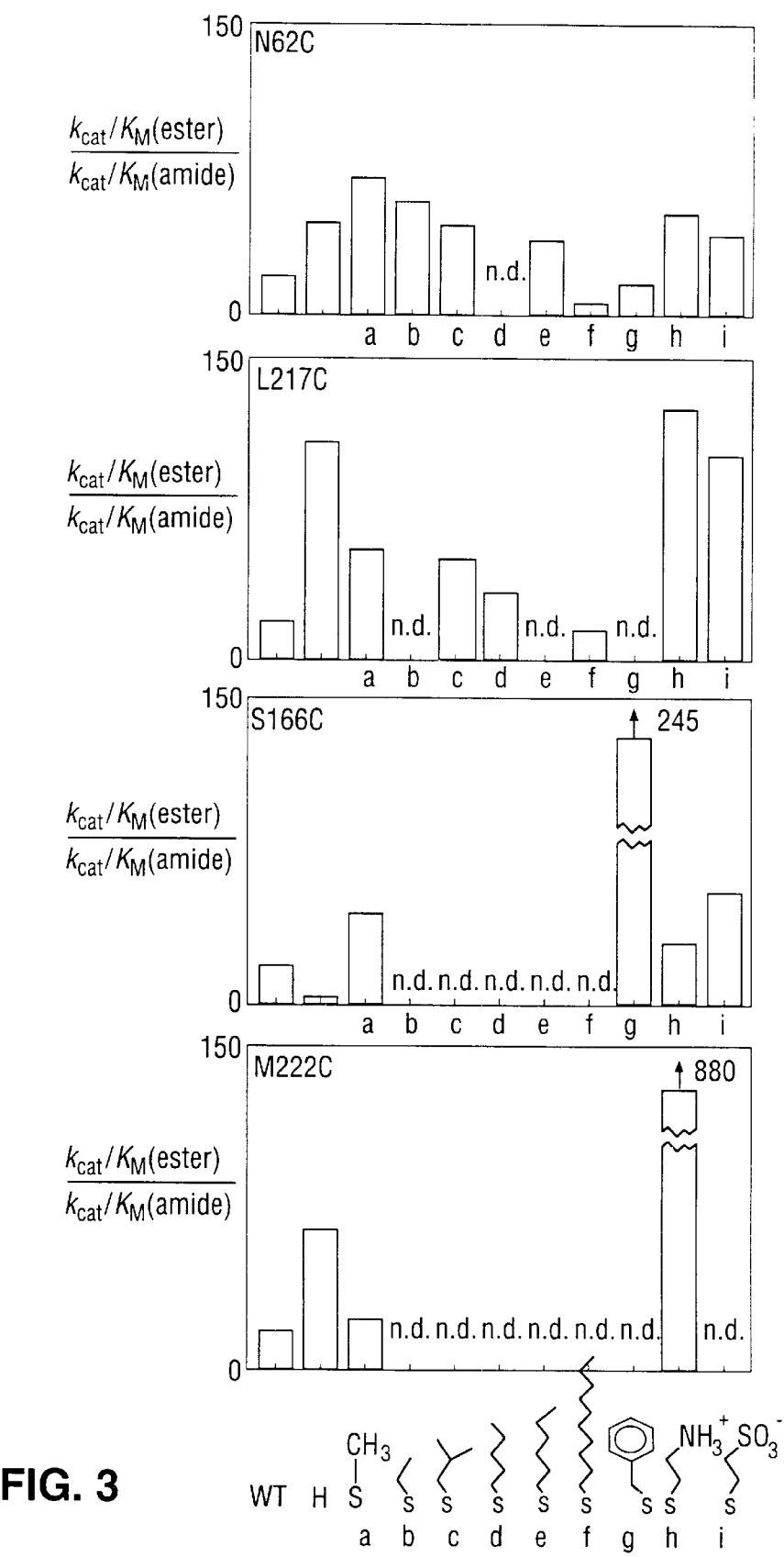
FIG. 3 shows the ratio of $k_{cat}/K_M$ constants for esterase-to-amidase activity. Esterase and amidase activity was determined with succinyl-alanine-alanine -proline-phenylalanine-thiobenzyl ester ("suc-AAPF-SBn") and succinyl-alanine-alanine -proline-phenylalanine-paranitroanalide ("suc-AAPF-pNA") substrates, respectively. All chemically modified mutants had the structure enzyme-$CH_2$—S—R, where the structure of the various R groups investigated is shown. In the N62C family, the straight-chain alkyl group of intermediate length was hexyl (e) and in the L217C family it was pentyl (d); n. d.=not determined. For comparison, the ratio for the WT enzyme was 17.

Of the N62 MEs, all except N62C—S(CH$_2$)$_9$CH$_3$ (-f) exhibited improved esterase activity relative to WT. Even the N62 mutation to cysteine itself created a better esterase and poorer amidase than WT. Chemical modification of N62C enhanced the absolute esterase activity still further, to ≈3-fold greater than WT for N62C—SCH$_3$, (-a) and N62C—SCH$_2$CH$_3$, (-b). In fact, N62C—SCH$_2$CH$_3$, (-b) with its $k_{cat}/K_M$ of 11100±2300 $s^{-1}$ $mM^{-1}$ had the highest absolute esterase activity of all the MEs investigated. However, the larger R groups of N62C—SCH$_2$CH(CH$_3$)$_2$ (-c) to N62C—SCH$_2$C$_6$H$_5$ (-g) caused decreases in $k_{cat}$ and $k_{cat}/K_M$ for esterase catalysis, and steady increases in both $k_{cat}$ and $k_{cat}/K_M$ for amidase. Consequently, the ratio of $k_{cat}/K_M$ for esterase to amidase activity decreased 10-fold as the chain length of —R increased from N62C—SCH$_3$ (-a) to N62C—S(CH$_2$)$_9$CH$_3$ (-f) (FIG. 3). The positively and negatively charged MEs, N62C—SCH$_2$CH$_2$NH$_3^+$ (-h) and N62C—SCH$_2$CH$_2$SO$_3^-$ (-i) respectively, both exhibited higher esterase and lower amidase activity than WT, with the improvement in the esterase-to-amidase ratio being ≈3-fold regardless of the sign of the charge introduced. In addition, the larger R groups of N62C—SCH$_2$CH(CH$_3$)$_2$ to N62C—SCH$_2$C$_6$H$_5$ (-c to -g) elicited reduced $K_M$s for both ester and amide substrates. This demonstrates that hydrophobic interactions at the 62 site are beneficial to binding.

Figure 4:
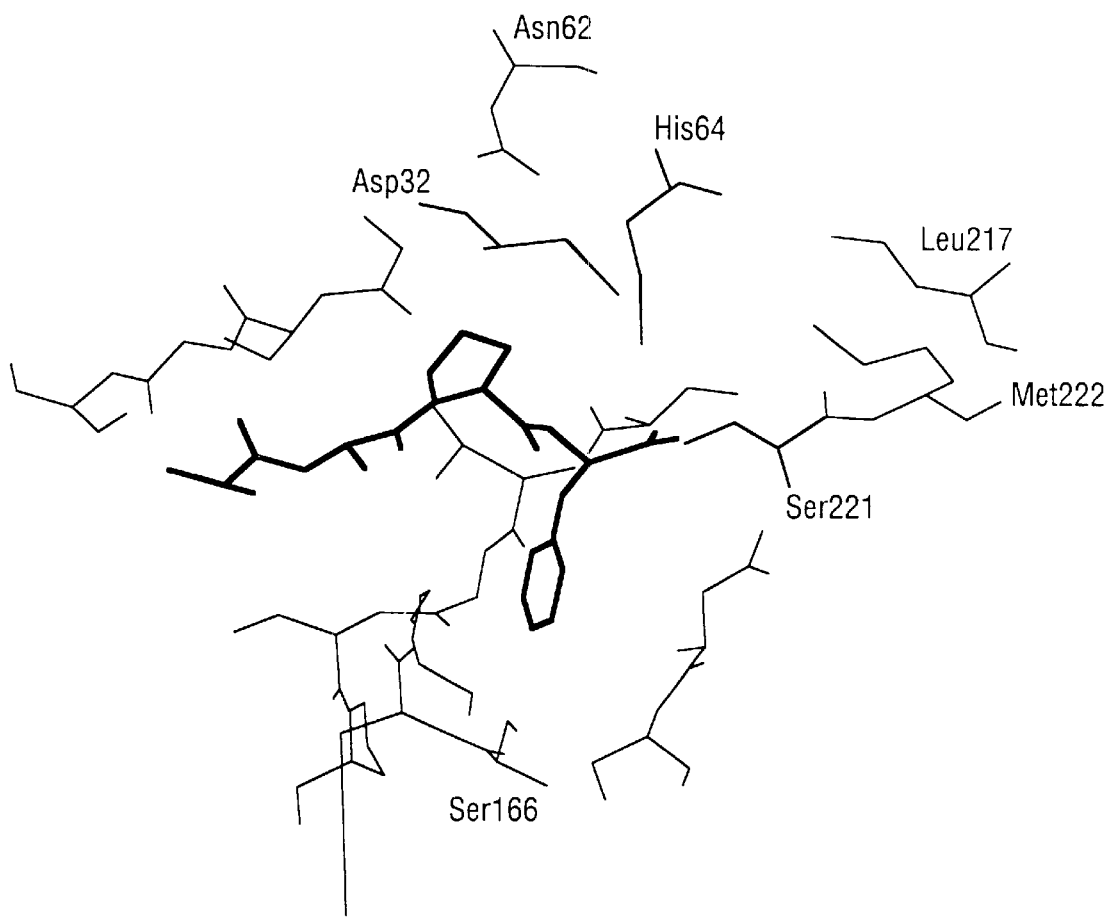
FIG. 4 shows the active site of subtilisin *Bacillus lentus* with sucAAPF (heavy black) bound. The catalytic triad and the four active site residues investigated are shown. Residue 62 is part of the $S_2$ pocket, residue 217 is at the mouth of the $S_1$'(leaving group) pocket, residue 166 is at the bottom of the $S_1$ pocket, and residue 222 is between the $S_1$ and $S_1$' pockets.

All of the L217C CMMs generated also exhibited improved esterase $k_{cat}/K_M$s compared to WT. At this site, mutation to cysteine alone again generated a superior catalyst having 1.5-fold better esterase and 4-fold poorer amidase activity than WT. However, its modification to L217C—SCH$_3$ (-a) caused a decrease in both esterase $k_{cat}$ and $k_{cat}/K_M$ compared to L217C itself. L217C—SCH$_2$CH(CH$_3$)$_2$ (-c) was the most active 217 esterase and exhibited a $k_{cat}/K_M$ of 7900±800 $s^{-1}$ $mM^{-1}$. While all of the 217 MEs exhibited greater than WT esterase activity, further increases in the chain length of —R from —S(CH$_2$)$_4$CH$_3$ to —S(CH$_2$)$_9$CH$_3$, (-d to -f) caused further decreases in $k_{cat}$ and $k_{cat}/K_M$. This is in contrast to the trend observed for amidase $k_{cat}$ and $k_{cat}/K_M$, values for the same MEs. Berglund et al., *J. Am. Chem. Soc.,* 119:5265–5266 (1997), which is hereby incorporated by reference. As a result, all of the L217C MEs except L217C—S(CH$_2$)$_9$CH$_3$ (-f) had higher than WT esterase to amidase selectivity (FIG. 3). The positively charged L217C—SCH$_2$CH$_2$NH$_3^+$ (-h) and negatively charged L217C—SCH$_2$CH$_2$SO$_3^-$ (-i) MEs also displayed higher than WT esterase activities, with L217C—SCH$_2$CH$_2$SO$_3^-$ (-i) having a 2.6-fold higher than WT esterase $k_{cat}$. Furthermore, at 5060 $s^{-1}$, this was the highest esterase $k_{cat}$ of all the MEs studied. The L217C—SCH$_2$CH$_2$NH$_3^+$ (-h) had a $(k_{cat}/K_M)ester/(k_{cat}/K_M)_{amide}$ ratio of 134, compared to 17 for WT. The correlations between decreased esterase and increased amidase activities with increasing chain length of —R, and improved esterase and decreased amidase for charged modifications, paralleled each other for both the L217C and N62C MEs. These equivalent trends are consistent with residues 217 and 62 being equidistant from His64 of the catalytic triad (See FIG. 4).

Modification of the S166C residue of the S$_1$ pocket, which is quite remote from the catalytic triad and from the S$_1$' leaving group site of both the ester or amide substrates, exerted large effects on esterase-to-amidase selectivity. The S166C mutant itself, with a $k_{cat}/K_M$ of 350 $s^{-1}$ $mM^{-1}$, had the lowest esterase activity of all the MEs evaluated. However, it also had somewhat decreased amidase activity, giving an esterase-to-amidase selectivity ratio of four, compared to 17 for WT. Apart from having the lowest $k_{cat}$ for esterase, S166C had a significantly higher $K_M$ for esterase than the WT and was one of few mutants for which $K_M$ (esterase) >$K_M$ (amidase). In contrast, modification of S166C to generate S166C—S—CH$_3$ (-a) increased esterase-to-amidase selectivity to 45, a ≈3-fold improvement relative to WT. The large hydrophobic benzyl group of S166C—S—CH$_2$C$_6$H$_5$ (-g) increased esterase-to-amidase selectivity still further to 245, which was 14-fold higher than WT, while the charged hydrophilic groups of S166C—SCH$_2$CH$_2$NH$_3^+$ (-h) and S166C—SCH$_2$CH$_2$SO$_3^-$ (i) induced little improvement in the esterase-to-amidase ratio. That the esterase $K_M$ decreased, while the amidase $K_M$ increased significantly, relative to WT for the S166C—S—CH$_2$C$_6$H$_5$ (-g) ME, implied long-range interactions between its S$_1$ and S$_1$' pockets and different rate-determining steps. These results complement those previously observed for the more hydrophilic G166N and G166S mutants of subtilisin BPN', both of which effected improved esterase and esterase-to-amidase activity relative to WT. Bonneau et al., *J. Am. Chem. Soc.,* 113:1026–1030 (1991), which is hereby incorporated by reference.

At the Met222 site, both M222C—SCH$_2$CH$_2$NH$_3^+$ (-h) and M222C exhibited an improved esterase $k_{cat}/K_M$ of up to 1.5, while all of M222C—S—CH$_3$ (-a), M222C—SCH$_2$CH$_2$NH$_3^+$ (-h), and M222C displayed up to 37-fold reduced amidase activity. The esterase-to-amidase activity of the cysteine parent, M222C, with its 4-fold improvement, was itself significantly higher than WT. The M222C mutant has a S$_1$' leaving group site that is less sterically congested than WT. This may enhance the rate of acyl-enzyme hydrolysis, which is often the rate-determining step for ester substrates. M222C—S—$CH_3$ (-a), which differs from WT only in the replacement of one of the methionine side-chain mehtylenes ($CH_2$) by sulfur, had the same $k_{cat}$ as WT, but an increased $K_M$. At this site, the most improved ME was M222C—$SCH_2CH_2NH_3^+$ (-h), which exhibited an esterase-to-amidase selectivity of 879, compared to 17 for the WT. This 52-fold improvement in esterase-to-amidase ratio of the series arose largely from a 31-fold lowered amidase $k_{cat}$, but with the WT level of esterase $k_{cat}$ being retained. This result was consistent with the observation that the M222K mutant of subtilisin BPN' caused improved esterase activity and severely decreased amidase activity, thus, generating an enzyme with greatly improved esterase-to-amidase specificity. Graycar et al., *Ann. N.Y. Acad. Sci.*, 672:71–79 (1992), which is hereby incorporated by reference.

With 19 of 25 MEs evaluated achieving the goal of better-than-WT esterase-to-amidase selectivity without diminishing the absolute esterase-rate, the ME approach was clearly broadly applicable. Overall, esterase-to-amidase specificity varied from 4-fold lower than WT for S166C to 52-fold higher than WT for M222C—$SCH_2CH_2NH_3^+$. At least one member from each of the four families of mutants studied met both criteria of excellent esterase activity and high esterase-to-amidase selectivity, with: N62C—$SCH_3$, (-a) being 3-fold, L217C—$SCH_2CH_2NH_3^+$ (-h) and L217C—$SCH_2CH_2SO_3^-$ (-i) 6 to 8-fold, S166C—$SCH_2C_6H_5$ (-g) was 14-fold, and M222C—$SCH_2CH_2NH_3^+$ (-h) was 52-fold improved in terms of esterase-to-amidase ratio relative to the WT enzyme. With up to 880-fold esterase to amidase selectivity achievable by the ME approach, the potential of chemically modified mutant subtilisins for peptide synthesis was expanded considerably.

Example 4

Peptide Synthesis Using S166C—$SCH_2C_6H_5$, S166C—$SCH_2$(p-COOH—$C_6H_4$), S166C—$SCH_2C_6F_5$, S166C—$SCH_2CH_2NH_3^+$, and M222C—$SCH_2CH_2NH_3^+$.

General Methods

WT-subtilisin *Bacillus lentus* and mutant enzymes, S166C and M222C were purified (Stabile et al., *Bioorg. Med. Chem. Lett.*, 6:2501–2506 (1996); Berglund et al., *Bioorg. Med. Chem. Lett.*, 6:2507–2512 (1996); and DeSantis et al., *Biochemistry*, 37:5698–5973 (1998), which are hereby incorporated by reference) and prepared as previously reported in DeSantis et al., *Biochemistry*, 37:5698–5973 (1998), which is hereby incorporated by reference. Protected amino acids were purchased from Sigma or Bachem and were used as received. All solvents were reagent grade and distilled prior to use. Thin layer chromatography analysis and purification were performed on pre-coated Merck Silica gel (60 F-254) plates (250 μm) visualized with UV light or iodine. $^1H$ and $^{13}C$ NMR spectra were recorded on a Varian Gemini 200 (200 MHz for $^1H$ and 50.3 MHz for $^{13}C$) or Unity 400 (400 MHz for $^1H$ and 100 MHz for $^{13}C$) and spectrometer and chemical shifts are given in ppm (δ) using $CDCl_3$ or DMSO-$d_6$ as an internal standard. High resolution mass spectra (HRMS) were recorded using Micromass ZAB-SE ($FAB^+$). Optical rotations were measured with a Perkin-Elmer 243B polarimeter.

General Procedure for Peptide Ligation

To a solution of amino acid acyl donor (0.1 mmol) in DMF (0.4 mL) and water (0.4 mL), glycinamide hydrochloride (0.3 mmol) or alaninamide hydrochloride (0.2 mmol) and $Et_3N$ (0.083–0.125 mL, 0.3–0.4 mmol) was added, followed by the addition of a solution of 1 mg of active enzyme (0.0037 mmol, 0.037 eq.), as determined by titration with phenylmethanesulfonyl fluoride (PMSF) (Hsia et al., *Anal. Biochem.*, 242:221–227 (1996), which is hereby incorporated by reference), in buffer solution (10 mmol MES, 1 mmol $CaCl_2$, pH 5.8). The resulting total volume of reaction was 1.0–1.2 mL. The reaction was left stirring at room temperature for the period of time indicated in Tables 2–4, below. Where D-amino acids were used as acyl donors, after 24 hours, 1 mg more of active enzyme as well as an equal amount of DMF were added. After the reaction was finished, the mixture was then concentrated in vacuo and subjected to purification using preparative TLC (5–10% MeOH in $CH_2Cl_2$).

Peptide Ligation of L-Amino Acids

Figure 5:
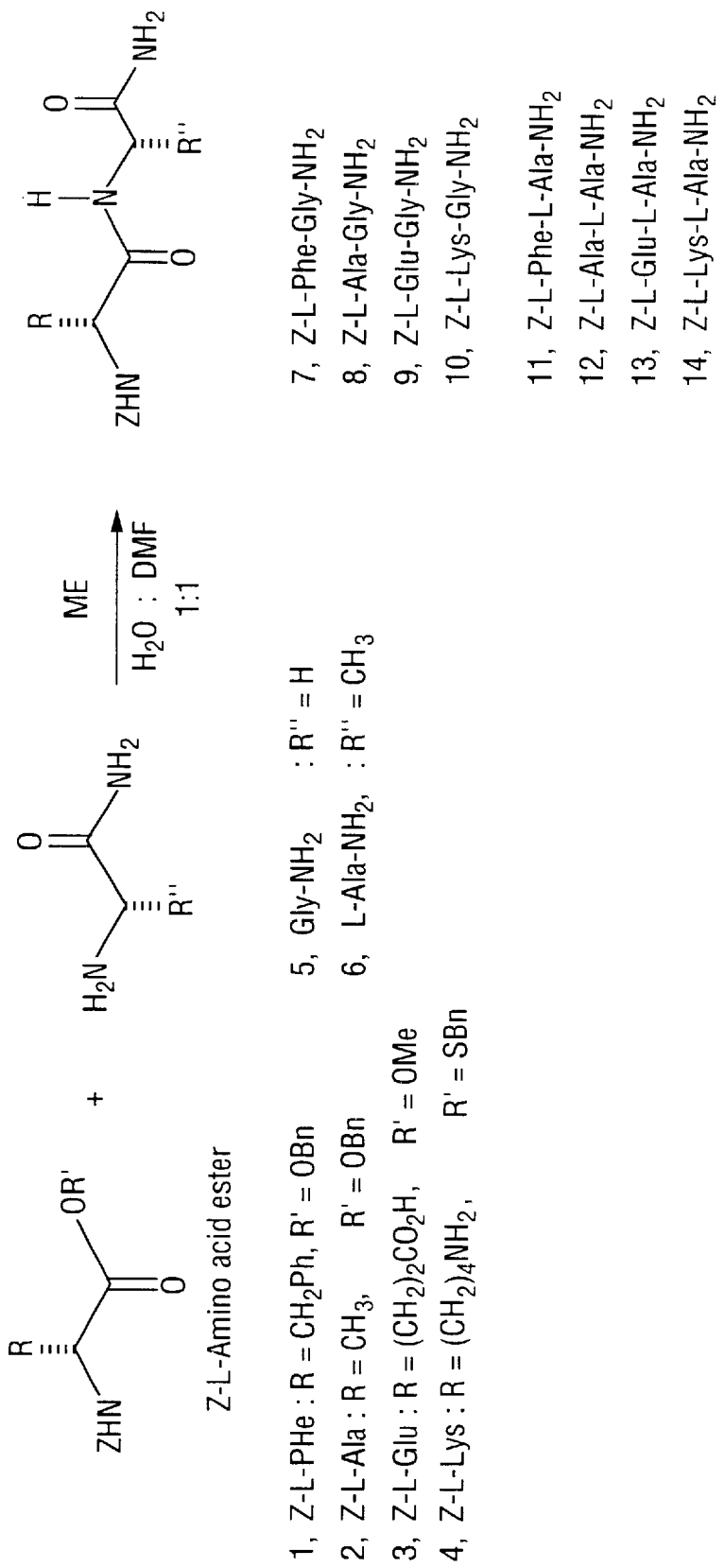
FIG. 5 shows the peptide ligation of L-amino acids using subtilisin *Bacillus lentus* modified enzymes.

Acyl donors Z-L-Phe-OBn, Z-L-Ala-OBn, Z-L-Glu-OMe, and Z-L-Lys-SBn (1–4) and acyl acceptors Gly-$NH_2$ and L-Ala-$NH_2$ (5, 6) were used for the coupling reaction as shown in FIG. 5. The acyl donors Z-L-Phe-OBn, Z-L-Ala-OBn, Z-L-Glu-OMe, and Z-L-Lys-SBn (1–4) provided representative examples of large and small hydrophobic, negatively charged and positively charged $P_1$ side chains, respectively and allowed a broad evaluation of the affinity of the $S_1$ pocket of these enzymes for various amino acids. The small amino acid amides Gly-$NH_2$ and L-Ala-$NH_2$ (5, 6) were chosen as the acyl acceptors since the $S_1'$ pocket of subtilisins is narrow (Moree et al., *J. Am. Chem. Soc.*, 119:3942–3947 (1997); Betzel et al., *J. Mol. Biol.*, 223:427–445 (1992); Sears et al., *J. Am. Chem. Soc.*, 116:6521–6530 (1994); and Jackson et al., *Science*, 266:243–247 (1994), which are hereby incorporated by reference), and, therefore, it accepts α-branched amino acids only poorly. The narrow nature of the $S_1'$ pocket is attributed to the bulky side chain of M222, this residue being a conserved residue amongst subtilisins. Siezen et al., *Protein Eng.*, 4:719–737 (1991), which is hereby incorporated by reference. This has limited their use in peptide ligation applications.

The coupling of Z-L-Phe-OBn (1), containing the preferred phenylalanine $P_1$ residue of SBL, with Gly-$NH_2$ (5) yielded dipeptide Z-L-Phe-Gly-$NH_2$ (7) in excellent yields using both SBL-WT and all four S166-MEs (Table 2, below) as catalysts after 1 hour. No reaction was observed in the absence of the enzyme. M222C—$SCH_2CH_2NH_3^+$ which had the highest esterase/amidase ratio gave the product in only 33% yield after 5 hours and starting material, Z-Phe-OBn (1), was recovered in 41% yield. Since M222C is located at the boundary between $S_1$ and $S_1'$ pockets, its modification apparently causes steric hindrance at the active site precluding substrate binding in the $S_1$ pocket.

TABLE 2

SBL-WT and SBL-ME-catalyzed coupling of L-amino acids (1–4) and glycinamide (5)[a]

| | Z-L-Phe-Gly-$NH_2$ (7) % yield | Z-L-Ala-Gly-$NH_2$ (8) % yield | | Z-Glu-Gly-$NH_2$ (9) % yield | | Z-Lys-Gly-$NH_2$ (10) % yield |
|---|---|---|---|---|---|---|
| MEs | 1 h | 1 h | 5 h | 1 h | 5 h | 5 h |
| WT | 92 | 68 | 91 | 64 | 62 | 83 |
| S166C-$SCH_2C_6H_5$ | 92 | 59 | 95 | 68 | 96 | 93 |
| S166C-$SCH_2C_6F_5$ | 93 | 42 | 94 | 61 | 61 | 71 |
| S166C-$SCH_2$(p-COOH—$C_6H_4$) | 100 | 38 | 82 | 30 | 62 | 99 |

TABLE 2-continued

SBL-WT and SBL-ME-catalyzed coupling of L-amino acids (1–4) and glycinamide (5)[a]

| MEs | Z-L-Phe-Gly-NH$_2$ (7) % yield | Z-L-Ala-Gly-NH$_2$ (8) % yield | | Z-Glu-Gly-NH$_2$ (9) % yield | | Z-Lys-Gly-NH$_2$ (10) % yield |
|---|---|---|---|---|---|---|
| | 1 h | 1 h | 5 h | 1 h | 5 h | 5 h |
| S166C—SCH$_2$CH$_2$NH$_3$$^+$ | 95 | 63 | 94 | 69 | 100 | 86 |
| M222C—SCH$_2$CH$_2$NH$_3$$^+$ | 33 (5 h) | — | — | — | 33 | — |

[a]conditions: 0.1 mmol of acyl donor, 0.3 mmol of glycinamide hydrochloride, 0.4 mmol of Et$_3$N, 1 mg of enzyme, 1:1 H$_2$O:DMF. The total volume of the reaction is 1.0–1.2 mL.

High yields were also obtained using Z-L-Ala-OBn (2) as the acyl donor with WT and each of MEs but required a longer reaction time of 5 hours. The yields obtained after running the reaction for 1 hour were all lower and in all cases starting material was recovered. The requirement for a longer reaction time in this case, compared to using Z-L-Phe-OBn (1) as the acyl donor, is consistent with SBL-WT's preference for substrate binding of large hydrophobic over small group P$_1$ substituents in the S$_1$ subsite. Gron et al., Biochemistry, 31:6011–6018 (1992), which is hereby incorporated by reference.

When Z-Glu-OMe (3) with its negatively charged P$_1$ residue, was used as the acyl donor, only moderate yields of Z-Glu-Gly-NH$_2$ (9) were obtained after 1 hour in all cases. Unlike the reaction of acyl donor Z-L-Ala-OBn (2), prolonging the reaction time led to an improved yield in the case of S166C—SCH$_2$C$_6$H$_5$, —SCH$_2$(p-COOH—C$_6$H$_4$), and —SCH$_2$CH$_2$NH$_3$$^+$. The yields using SBL-WT and S166C—SCH$_2$C$_6$F$_5$ as catalysts after 5 hours were virtually the same as for 1 hour. However, it was possible to isolate Z-L-Glu-Gly-NH$_2$ (9) in quantitative yield using S$_{166}$C—SCH$_2$CH$_2$NH$_3$$^+$ with its complementary charged S$_1$ pocket. When using M222C—SCH$_2$CH$_2$NH$_3$$^+$ as the catalyst, no enhancement of yield was observed with respect to the SBL-WT catalyzed reaction. This reaction yielded only 33% of Z-L-Glu-Gly-NH$_2$ (9) after 5 hours in addition to 32% of the recovered starting material Z-L-Glu-OMe (3). As mentioned above, the M222 residue seems to inhibit the binding substrates P$_1$ residue in S$_1$ pocket of the enzyme. This may be the cause for the low yield when using this ME and correlates with the recovery of starting material. Z-L-Glu-Gly-NH$_2$ (9) was also obtained in excellent yield (96%) using S166C—SCH$_2$C$_6$H$_5$ as the catalyst.

Enhanced turnover of the positively charged Z-L-Lys-SBn (4) acyl donor with the charged ME, S166C—SCH$_2$(p-COOH—C$_6$H$_4$), was observed resulting in 99% of Z-L-Lys-Gly-NH$_2$ (10), the best result of the series. Again, a good yield of 93% of Z-L-Lys-Gly-NH$_2$ (10) was also observed using S166C—SCH$_2$C$_6$H$_5$ as the catalyst. This may be due to the high esterase/amidase ratio of this enzyme. The reaction using S166C—SCH$_2$C$_6$F$_5$ gave only 71% yield of product which was lower than the reaction using WT as the catalyst. A higher yield, with respect to WT, was also obtained using S$_{166}$C—SCH$_2$CH$_2$NH$_3$$^+$ in spite of the potential electrostatic repulsion between the modified enzyme and the side chain of Lys.

The synthetic ability of the selected MEs using other acyl acceptors other than Gly-NH$_2$ was further investigated. Since the S$_1$' pocket of subtilisin is small and restricted, the smallest α-branched amino acid, Ala-NH$_2$ (6), was used to probe this subsite (See Table 3).

TABLE 3

SBL WT and ME-catalyzed coupling of L-amino acids (1–4) and L-alaninamide (6)[a]

| MEs | Z-L-Phe-Ala-NH$_2$ (11) % yield | Z-L-Ala-Ala-NH$_2$ (12) % yield | Z-L-Glu-Ala-NH$_2$ (13) % yield | Z-L-Lys-Ala-NH$_2$ (14) % yield |
|---|---|---|---|---|
| WT | 57 | 0 | 0 | 0 |
| S166C—SCH$_2$C$_6$H$_5$ | 51 | 0 | 0 | 0 |
| S166C—SCH$_2$C$_6$F$_5$ | 33 | 0 | 0 | 0 |
| S166C—SCH$_2$(p-COOH—C$_6$H$_4$) | 48 | 0 | 0 | 0 |
| S166C—SCH$_2$CH$_2$NH$_3$$^+$ | 88 | 16 | 14 | 0 |
| M222C—SCH$_2$CH$_2$NH$_3$$^+$ | 22 | 0 | 0 | 0 |

[a]conditions: 0.1 mmol of acyl donor, 0.2 mmol of alaninamide hydrochloride, 0.3 mmol of Et$_3$N, 1 mg of enzyme, 1:1 H$_2$O:DMF, 24 h. The total volume of the reaction is 1.0–1.2 mL.

In all cases, the reaction of L-Ala-NH$_2$ (6) with Z-L-Phe-OBn (1) was slower than Gly-NH$_2$ (5) with Z-L-Phe-OBn (1). Further, after 24 hours, Z-L-Phe-Ala-NH$_2$ (11) was obtained in moderate yield (33–57%) using WT, S166C—SCH$_2$C$_6$H$_5$, —SCH$_2$C$_6$F$_5$, and —SCH$_2$(p-COOH—C$_6$H$_4$) as the catalysts. However, Z-L-Phe-Ala-NH$_2$ (11) was obtained in 88% yield in the case of S166C—SCH$_2$CH$_2$NH$_3$$^+$. Unlike S166C—SCH$_2$CH$_2$NH$_3$$^+$, the use of M222C—SCH$_2$CH$_2$NH$_3$$^+$ did not improve the yield of the dipeptide product as compared to the WT-catalyzed reaction; only a low 22% yield of Z-L-Phe-Ala-NH$_2$ (11) was obtained. This was possibly due to the steric interaction of this residue at the binding site, S$_1$pocket, with the P$_1$ substrate as mentioned above.

When Z-L-Ala-OBn (2) or Z-L-Glu-OMe (3) were used as acyl donors, no reaction was observed with L-Ala-NH$_2$ (6) for five out of the six enzymes used. However, when S166C—SCH$_2$CH$_2$NH$_3$$^+$ was used as the catalyst, the yield of dipeptides Z-Ala-Ala-NH$_2$ (12) and Z-Glu-Ala-NH$_2$ (13) were formed in 16% and 14%, respectively. While these yields were low, they represented a dramatic improvement over WT.

No reaction was observed by treatment of Z-L-Lys-SBn (4) and L-Ala-NH$_2$ (6) with WT and all MEs, including using the negative charged ME, S166C—SCH$_2$(p-COOH—C$_6$H$_4$), in which case the complementary electrostatic interaction was expected.

These results contrast to the previously reported preference for Ala over Gly in the S$_1$' pocket of subtilisin Bacillus lentus. Gron et al., Biochemistry, 31:6011–6018 (1992), which is hereby incorporated by reference. This preference was not observed: the yields obtained using glycinamide (5) as the acyl acceptor were higher in all cases, and the reaction times were shorter (Table 2) compared to using alaninamide (6) (Table 3) as the acyl acceptor.

D-Amino Acid Ligation

Figure 6:
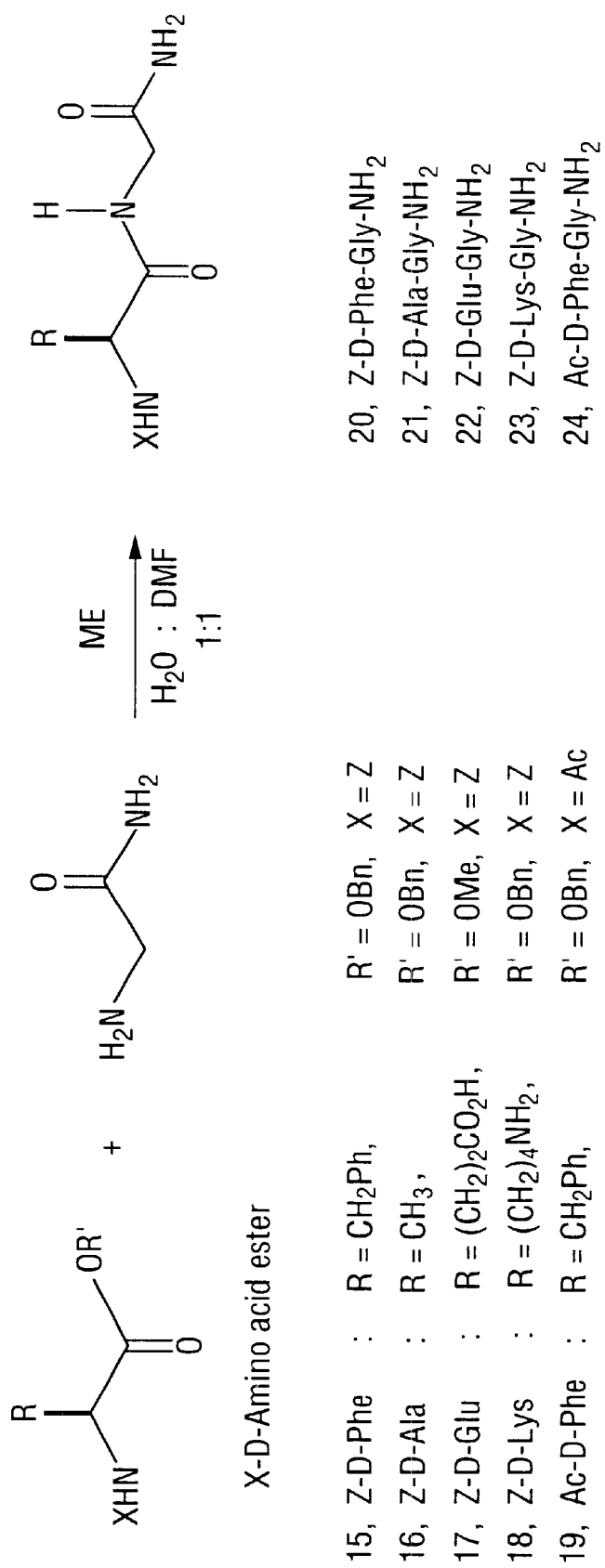
FIG. 6 shows the peptide ligation of D-amino acids using subtilisin *Bacillus lentus* modified enzymes.

Next, the scope of application of SBL catalyzed peptide ligation was extended to include D-amino acid esters Z-D-Phe-OBn, Z-D-Ala-OBn, Z-D-Glu-OMe, Z-D-Lys-OBn, and Ac-D-Phe-OBn (15–19) as the acyl donors (FIG. 6) by the ME methodology, which was not possible with SBL-WT. The results are shown in Table 4.

TABLE 4

SBL WT and ME-catalyzed coupling of D-amino acids (15–19) and glycinamide (5)[a]

| MEs | Z-D-Phe-Gly-NH$_2$ (20) % yield | Z-D-Ala-Gly-NH$_2$ (21) % yield | Z-D-Glu-Gly-NH$_2$ (22) % yield | Z-D-Lys-Gly-NH$_2$ (23) % yield | Ac-D-Phe-Gly-NH$_2$ (24) % yield |
|---|---|---|---|---|---|
| WT | 0 | 0 | 0 | 0 | 0 |
| S166C-SCH$_2$C$_6$H$_5$ | 66 | 50 | 3 | 0 | 15 |
| S166C-SCH$_2$C$_6$F$_5$ | 39 | 49 | 3 | 0 | 27 |
| S166C-SCH$_2$(p-COOH—C$_6$H$_4$) | 35 | 48 | 6 | 0 | 34 |
| S166C-SCH$_2$CH$_2$NH$_3^+$ | 43 | 45 | 10 | 0 | 38 |

[a]conditions: 0.1 mmol of acyl donor, 0.3 mmol of glycinamide hydrochloride, 0.4 mmol of Et$_3$N, 1 mg of enzyme, 1:1 H$_2$O:DMF, 48 h. After 24 h, another 1 mg of enzyme was added. The total volume of the reaction is 1.5–3.0 mL.

For accurate comparison, the D-isomers Z-D-Phe-OBn, Z-D-Ala-OBn, Z-D-Glu-OMe, Z-D-Lys-OBn, and Ac-D-Phe-OBn (15–19) of the representative L-amino acids Z-L-Phe-OBn, Z-L-Ala-OBn, Z-L-Glu-OMe, and Z-L-Lys-SBn (1–4) examined in the previous ligation examples were used. The stereoselectivity of SBL-WT for L-amino acids was clear (Table 4), because none of the D-amino acid esters evaluated gave dipeptide products with WT as the catalyst. All of the S166C-MEs yielded dipeptide products containing D-amino acids Z-D-Phe-Gly-NH$_2$, Z-D-Ala-Gly-NH$_2$, Z-D-Glu-Gly-NH$_2$, Z-D-Lys-Gly-NH$_2$, and Ac-D-Phe-Gly-NH$_2$ (20–24). While each of these enzymes still showed a preference for L-amino acids, yields of up to 66% of Z-D-Phe-Gly-NH$_2$, using S166C—SCH$_2$C$_6$H$_5$, over 0% for WT, demonstrated a dramatic improvement in SBL's acceptance of D-amino acids.

Similar yields of Z-D-Ala-Gly-NH$_2$ (21) were obtained using Z-D-Ala-OBn (16) as the acyl acceptor from all four S166C-MEs catalyzed reactions. This demonstrated that chemical modification at this residue broadened stereospecificity of the S$_1$ pocket in general manner.

When Z-D-Glu-OMe (17) was used as the acyl donor, only a low yield of dipeptide Z-D-Glu-Gly-NH$_2$ (22) was obtained in all ME catalyzed reactions. The best yield, 10% of Z-D-Glu-Gly-NH$_2$ (22), resulted using S166C—SCH$_2$CH$_2$NH$_3^+$. This may be accounted for by complementary electrostatic interaction between the side chain of S166C—SCH$_2$CH$_2$NH$_3^+$ and the side chain of glutamic acid acyl donors. In contrast, no product was observed when Z-D-Lys-OBn (18) was used as the acyl donor for all WT and ME catalyzed reactions, including the use of S166C—SCH$_2$(p-COOH—C$_6$H$_4$) as the catalyst in which case a great improvement in yield in the reactions of Z-L-Lys-SBn was observed.

Figure 7:
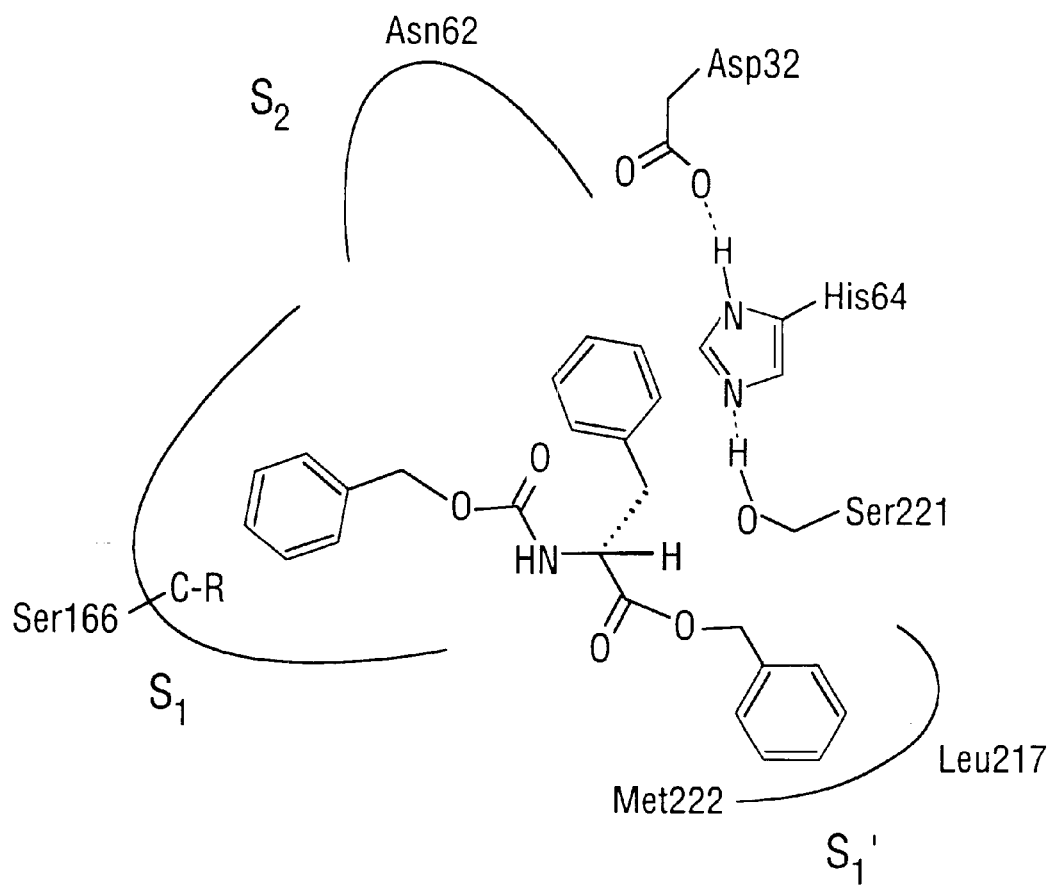
FIG. 7 shows the proposed binding of the Z-protecting group of Z-D-Phe-OBn with subtilisin *Bacillus lentus*. The large hydrophobic carbobenzoxy protecting (Z) group is binding in the $S_1$ pocket instead of the D-phenylalanine side chain.

Since Z-D-Phe-OBn (15) as the acyl donor gave 35–66% of product with each of the MEs evaluated and 0% yield with WT and furthermore, since replacing the carbobenzoxy (Z) group of Z-D-Phe-OBn (15) with the acetyl group in the acyl donor Ac-D-Phe-OBn (19) resulted in lower yields (Table 4), it is speculated that the carbobenzoxy group in Z-D-Phe-OBn (15) may direct binding in the S$_1$ pocket as shown in FIG. 7, a process not observed in Ac-D-Phe-OBn (19).

Dipeptides Produced

Z-Phe-Gly-NH$_2$ (7) (Moree et al., *J. Am. Chem. Soc.*, 119:3942–3947 (1997) and Morihara et al., *Biochem. J.*, 163:531–542 (1977), which are hereby incorporated by reference): $^1$H NMR (CDCl$_3$) δ3.10 (m, 2H, CH$_2$Ph), 3.85 (2×d, J=2, 5 Hz, 2H, NHCH$_2$CO), 4.40 (m, 1H, NHCHCO), 5.05 (s, 2H, OCH$_2$Ph), 5.50, 5.70, 6.25, 6.90 (4×brs, 4H, NH), 7.20–7.40 (m, 10H, 2×Ph); $^{13}$C NMR (CDCl$_3$) δ38.2, 42.7, 56.6, 67.3, 127.2, 128.1, 128.3, 128.6, 128.8, 129.2, 135.8, 136.0, 156.3, 171.2, 171.6. HRMS (FAB$^+$) MH$^+$ calcd 356.1610, found 356.1613. [α]$^+$$_D$=−4.3 (c 0.81, MeOH).

Z-Ala-Gly-NH$_2$ (8) (Bodanszky et al., *Int. J. Peptide Protein Res.*, 26:550–556 (1985), which is hereby incorporated by reference): $^1$H NMR (CDCl$_3$) δ1.40 (d, J=7 Hz, 3H, CH$_3$), 3.85 (dd, J=1.7, 5 Hz, 2H, NCH$_2$CO), 4.20 (m, 1H, NHCHCO), 5.10 (dd, J=1.6, 2 Hz, 2H, OCH$_2$Ph), 5.80, 6.60, 7.20 (3×brs, 4H, NH), 7.30–7.40 (m, 5H, Ph); $^{13}$C NMR (CDCl$_3$) δ17.7, 42.2, 50.6, 66.2, 127.6, 128.0, 136.0, 155.9, 171.3, 172.8. HRMS (FAB$^+$) MH$^+$ calcd 280.1297, found 280.1310. [α]$^{26}$$_D$=−8.44 (c 0.97, MeOH); lit. [α]$^{23}$$_D$=−8.5 (c 2, MeOH).

Z-Glu-Gly-NH$_2$ (9) (Schon et al., *Int. J. Peptide Protein Res.*, 22:92–109 (1983), which is hereby incorporated by reference): $^1$H NMR (DMSO-d$_6$) δ1.75–1.95 (m, 2H, CH$_2$CH$_2$COOH), 2.30 (m, 2H, CH$_2$CH$_2$COOH), 3.65 (dd, J=0.5, 1.7 Hz, 2H, NHCH$_2$CO), 4.10 (m, 1H, NHCHCO), 5.00 (s, 2H, OCH$_2$Ph), 7.20–7.40 (m, 5H, Ph), 12.40 (brs, 1H, COOH); $^{13}$C NMR (DMSO-d$_6$) δ27.2, 30.3,41.9, 54.2,65.6, 128.4, 128.5, 128.7, 128.8, 136.9, 156.2, 170.8, 171.7, 174.0 HRMS (FAB$^+$) MH$^+$ calcd 338.1352, found 338.1332. [α]$^{28}$$_D$=−10.2 (c 1.16, MeOH); lit. [α]$^{25}$$_D$=−10.2 (c, 1.0, MeOH).

Z-L-Lys-Gly-NH$_2$ (10): $^1$H NMR (DMSO-d$_6$) δ1.50 (m, 2H, CH$_2$(CH$_2$)$_3$NH$_2$), 1.60–1.85 (m, 4H, CH$_2$CH$_2$CH$_2$CH$_2$NH$_2$), 2.00–2.18 (m, 2H, (CH$_2$)$_3$CH$_2$NH$_2$) 3.30 (m, 2H, NHCH$_2$CO), 4.40 (m, 1H, NHCHCO), 5.10 (s, 2H, OCH$_2$Ph), 6.05, 6.20 (2×brs, 2H, NH), 7.20–7.40 (m, 5H, Ph); $^{13}$C NMR (DMSO-d$_6$) δ28.1, 29.0, 32.2, 42.3, 45.9, 53.8, 66.7, 128.1, 128.6, 136.7, 155.6, 172.2, 175.3. HRMS (FAB$^+$) MH$^+$ calcd 337.1876, found 337.1842. [α]$^{28}$$_D$=+6.97 (c 0.55, MeOH).

Z-L-Phe-L-Ala-NH$_2$ (11) (Morihara et al., *Biochem. J.*, 163:531–542 (1977) and Brubacher et al., *Can J. Biochem.*, 57:1054–1072 (1979), which are hereby incorporated by reference): $^1$H NMR (DMSO-d$_6$) δ1.20 (d, J=7 Hz, 3H, CH$_3$), 2.90 (m, 2H, CH$_2$Ph), 4.30 (m, 2H, 2×NHCHCO), 4.90 (s, 2H, OCH$_2$Ph), 5.75, 6.10, 6.45 (3×brs, 4H, NH), 6.90–7.40 (m, 10H, 2×Ph); $^{13}$C NMR (DMSO-d$_6$) δ18.5, 37.4, 48.1, 56.2, 66.2, 126.3, 127.4, 127.7, 128.1, 128.3, 129.2, 137.1, 138.2, 155.9, 171.2, 174.1. HRMS (FAB$^+$) MH$^+$ calcd 370.1766, found 370.1753. [α]$^{29}$$_D$=−8.86 (c 0.57, MeOH).

Z-L-Ala-L-Ala-NH$_2$ (12) (Katakai et al., *Macromolecules*, 6:827–831 (1973), which is hereby incorporated by reference): $^1$H NMR (DMSO-d$_6$) δ1.20 (2×d, J=7 Hz, 6H, 2×CH$_3$), 4.10, 4.20 (m, 2H, 2×NHCHCO), 5.00 (s, 2H, OCH$_2$Ph), 7.20–7.40 (m, 5H, Ph); $^{13}$C NMR (DMSO-d$_6$)

δ18.1, 18.4, 47.9, 50.1, 65.4, 127.7, 128.4, 137.0, 155.8, 172.0, 174.1. HRMS (FAB$^+$) MH$^+$ calcd 294.1454 found 294.1457. $[\alpha]^{25}{}_D$=−20.4 (c 0.77, MeOH).

Z-L-Glu-L-Ala-NH$_2$ (13): $^1$H NMR (DMSO-d$_6$) δ1.20 (d, J=7 Hz, 3H, CH$_3$), 1.82–2.00 (m, 2H, CH$_2$CH$_2$COOH), 2.30 (m, 2H, CH$_2$CH$_2$COOH), 4.00, 4.20 (m, 2H, 2×NHCHCO), 5.00 (s, 2H, OCH$_2$Ph), 6.20–7.40 (m, 5H, Ph); $^{13}$C NMR (DMSO-d$_6$) δ18.4, 26.2, 30.2, 47.9, 53.1, 65.4, 126.5, 127.7, 127.8, 128.1, 128.4, 137.0, 156.2, 173.6, 173.8, 174.1. HRMS (FAB$^+$) MH$^+$ calcd 352.1509, found 352.1478. $[\alpha]^{25}{}_D$=−16.7 (c 0.76, MeOH).

Z-D-Phe-Gly-NH$_2$ (20): $^1$H and $^{13}$C NMR data are identical to (7). HRMS (FAB$^+$) MH$^+$ calcd 356.1610 found 356.1608; $[\alpha]^{30}{}_D$=+4.12 (c 1.17, MeOH).

Z-D-Ala-Gly-NH$_2$ (21) (Richman et al., *Int. Peptide Protein Res.*, 25:648–662 (1985), which is hereby incorporated by reference): $^1$H and $^{13}$C NMR data are identical to (8). HRMS (FAB$^+$) MH$^+$ calcd 280.1297 found 280.1298; $[\alpha]^{27}{}_D$+10.5 (c 0.72, MeOH); lit. $[\alpha]_D$=+10.5.

Z-D-Glu-Gly-NH$_2$ (22): $^1$H and $^{13}$C NMR data are identical to (9). HRMS (FAB$^+$) MH$^+$ calcd 338.1352 found 338.1348; $[\alpha]^{28}{}_D$=+10.77 (c 1, MeOH).

Ac-D-Phe-Gly-NH$_2$ (24) (Thompson et al., *J. Med. Chem.*, 29:104–111 (1986), which is hereby incorporated by reference): $^1$H NMR (DMSO-d$_6$) δ1.90 (S, 3H, CH$_3$), 3.05 (m, 2H, NHCH$_2$CO), 3.65 (2×d, J=7, 15 Hz, 2H, CHCH$_2$Ph), 4.40 (q, J=7Hz, 1H NHCHCO), 7.15–7.25 (m, 5H, Ph); $^{13}$C NMR (DMSO-d$_6$) δ22.4, 29.1, 45.9, 54.7, 126.1, 127.9, 128.9, 137.3, 155.2, 171.2, 171.5. HRMS (FAB$^+$) MH$^+$ calcd 264.1348, found 264.1321. $[\alpha]^{30}{}_D$=−4.38 (c 0.80, MeOH).

Example 5

Peptide Synthesis Using Chemically Modified Mutant Enzymes with Polar Substituents, Such as Oxazolidinones, Alkyl Amino Groups with Positive Charge, and Saccharides General Methods $^1$H and $^{13}$C NMR spectra were measured on a Varian Unity (400 MHz for $^1$H and 100 MHz for $^{13}$C) spectrometer with DMSO-d$_6$ as internal standard. High resolution mass spectra ("HRMS") were recorded using Micromass ZAB-SE (FAB$^+$). Optical rotations were measured with a Perkin-Elmer 243B polarimeter. ALUGRAM® SIL G/UV254 Art.-Nr. 818 133 (Macherey-Nagel GmbH & Co., Duren, Germany) was used for analytical TLC. Preparative TLC was performed on pre-coated Silica gel plate Art.5744 (Merck, Gibbstown, N.J.) visualized with UV light. WT-subtilisin *Bacillus lentus* and mutant enzymes were purified and prepared as reported in Stabile et al., *Bioorg. Med. Chem. Lett.*, 6:2501–2506 (1996) and DeSantis et al., *Biochemistry*, 37:5968–5973 (1998), which are hereby incorporated by reference, and as described in Example 1. Protected acids were purchased from Sigma-Aldrich Inc. (Milwaukee, Wis.) or Bachem Inc. (Torrance, Calif.) and were used as received. All solvents were reagent grade and distilled prior to use.

General Procedure for Peptide Ligation

To a solution of Z-L-Phe-OBn (25, 19.2 mg, 0.05 mmol) in DMF (0.25 mL) and water (0.144 mL), glycinamide hydrochloride (31, 17 mg, 0.15 mmol) and Et$_3$N (0.15 mmol, 0.0625 mL) were added, followed by the addition of S166C—S-inden-oxaz(S,R) (ME-n, 0.106 mL, 0.5 mg of active enzyme in 10 mM MES buffer (pH 5.8) including 1 mM CaCl$_2$). The reaction was stirred for one hour at room temperature. The mixture was diluted with AcOEt and washed with 1 M KHSO$_4$ (1 mL×1) and brine (1 mL×1), and the organic layer was dried over MgSO$_4$. After evaporation, the residue was purified by preparative TLC (CH$_2$Cl$_2$/MeOH=90/10) to afford Z-L-Phe-Gly-NH$_2$ (33, 17.8 mg, quantitative).

Peptide ligations of other substrates using other enzymes were carried out following the same procedure except for reaction time. In the case of D-amino acids as acyl donors, 0.5 mg more active enzymes was added to the reaction vessel after 24 hours, and then the mixture was stirred for another 24 hours.

Peptide Ligation of L-Amino Acids

Figure 8:
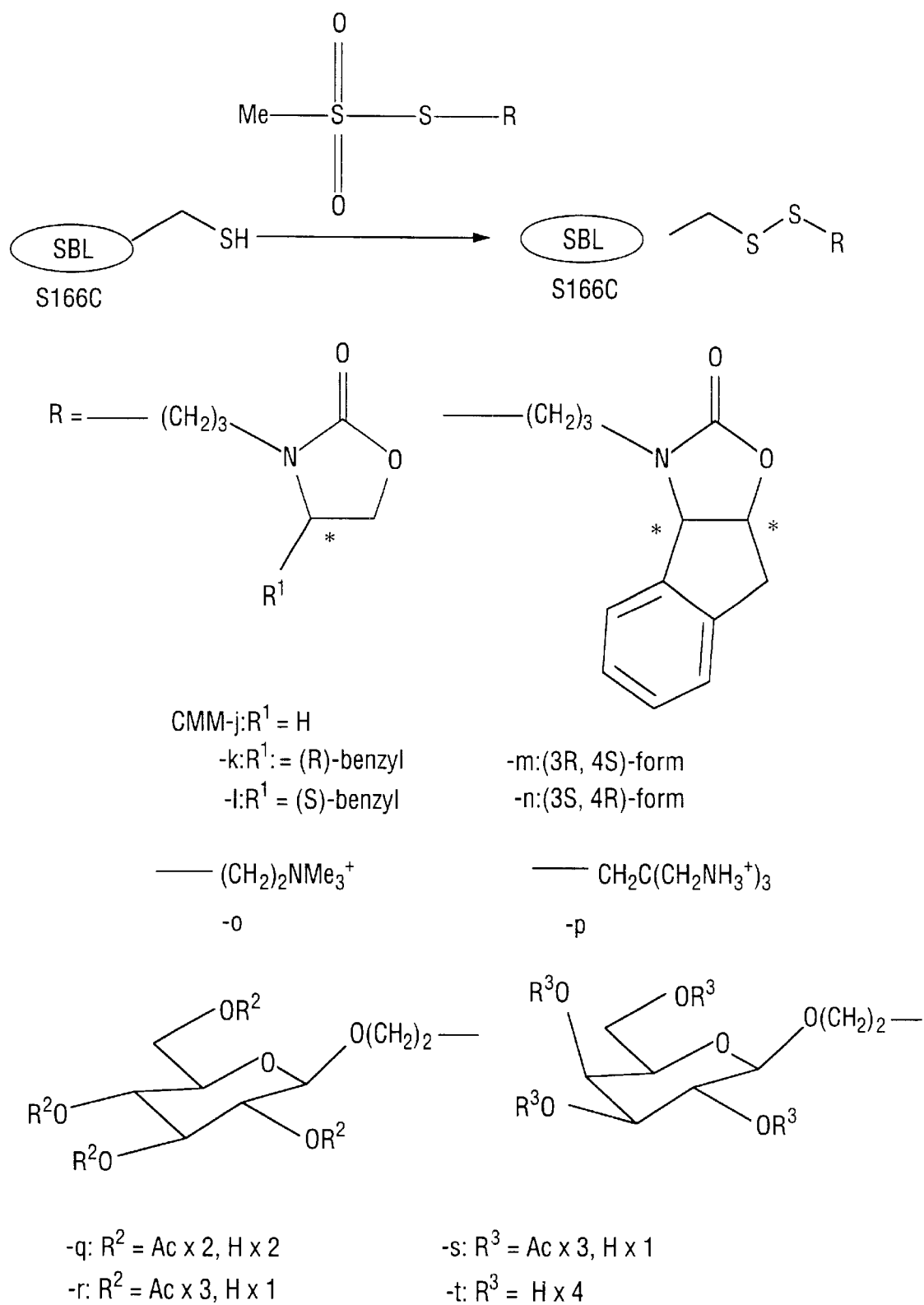
FIG. 8 shows the chemical modification of S166C mutants of subtilisin *Bacillus lentus* to generate modified enzymes.

First, the coupling reaction of L-amino acid, Z-L-Phe-OBn (25), Z-L-Ala-OBn (26), and Z-L-Glu-OMe (27), with glycinamide (31) were investigated as standard reactions (See FIGS. 1 and 8, Table 5).

TABLE 5

WT and MEs of SBL Catalyzed Peptide Coupling[a]

| acyl donor | acyl acceptor | product | time/h | WT | ME-j | -k | -l | -m | -n | -o | -p | -q | -r | -s | -t |
|---|---|---|---|---|---|---|---|---|---|---|---|---|---|---|---|
| Z-L-PheOBn (25) | GlyNH$_2$ · HCl (31) | Z-L-PheGlyNH$_2$ (33) | 1 | 92 | 92 | 86 | 88 | 82 | 100 | 74 | 75 | 95 | 93 | 91 | 95 |
| Z-L-AlaOBn (26) | 31 | Z-L-AlaGlyNH$_2$ (34) | 5 | 91 | 82 | 87 | 88 | 91 | 95 | 99 | 91 | 85 | 77 | 92 | 83 |
| Z-L-GluOMe (27) | 31 | Z-L-GluGlyNH$_2$ (35) | 5 | 62 | 67 | 60 | 54 | 68 | 56 | 63 | 71 | 58 | 65 | 54 | 67 |
| Z-D-PheOBn (28) | 31 | Z-D-PheGlyNH$_2$ (36) | 48[b] | 0 | 9 | 8 | 12 | 7 | 14 | 4 | 4 | 6 | 8 | 7 | 8 |
| Z-D-AlaOBn (29) | 31 | Z-D-AlaGlyNH$_2$ (37) | 48[b] | 0 | 61 | 86 | 80 | 86 | 80 | 79 | 73 | 80 | 77 | 72 | 70 |
| Z-D-GluOBn (30) | 31 | Z-D-GluGlyNH$_2$ (38) | 48[b] | 0 | 64 | 62 | 60 | 62 | 52 | 74 | 64 | 63 | 62 | 64 | 64 |
| 25 | L-AlaNH$_2$ · HCl (32) | Z-L-Phe-L-AlaNH$_2$ (39) | 24[c] | 57 | 50 | 31 | 30 | 33 | 37 | 44 | 36 | 28 | 34 | 31 | 32 |
| 26 | 32 | Z-L-Ala-L-AlaNH$_2$ (40) | 24[c] | 0 | 10 | 12 | 19 | 21 | 20 | 14 | 11 | 15 | 16 | 22 | 11 |
| 27 | 32 | Z-L-Glu-L-AlaNH$_2$ (41) | 24[c] | 0 | 64 | 60 | 59 | 61 | 59 | 58 | 60 | 48 | 50 | 51 | 55 |

[a] The reaction was performed in DMF/Water (1/1, v/v) using 0.1 M acyl donor, 0.3 M acyl acceptor, and 0.3 M Et$_3$N in the presence of 0.5 mg of active enzyme in 10 mM MES buffer (pH 5.8) containing 1 mM CaCl$_2$ at rt unless otherwise noted. Under same conditions, spontaneous hydrolysis or aminolysis did not occur.
[b] After 24 h, 0.5 mg of active enzyme was added and the mixture was stirred for another 24 h.
[c] In these cases, 0.2 M of 32 and 0.2 M of Et$_3$N were used.

The reactions were carried out using 0.5 mg of active enzyme with Et$_3$N in water solution containing 50% DMF. The activities of enzymes were determined by titration with phenylmethanesulfonyl fluoride ("PMSF"). Hsia et al., *Annal. Biochem.*, 242:221–227 (1996), which is hereby incorporated by reference. In all cases, the reactions smoothly proceeded to afford the corresponding dipeptides in good yields. These results indicated that the modification of S166C site by these substituents did not affect the essential ability to accept L-amino acids in peptide coupling.

Peptide Ligation of D-Amino Acids

Next, the extension of the use of the MEs to the coupling reaction of D-amino acids as acyl donor, Z-D-Phe-OBn (28), Z-D-Ala-OBn (29), and Z-D-Glu-OBn (30) with Z-L-Phe-OBn (1) was examined. While WT enzyme did not accept D-amino acids as acyl donors, all of the MEs were able to catalyze the coupling of D-amino acids with Z-L-Phe-OBn (1). Although the reactions of Z-D-Phe-OBn (28) in all cases were slow to give Z-D-Phe-Gly-NH$_2$ (39) in low yield (the best was 14% by using M-n), peptide coupling of Z-D-Ala-OBn (29) or Z-D-Glu-OBn (30) with Gly-NH$_2$ (31) proceeded without remaining substrates. It is noteworthy that using ME-k and -m in case of Z-D-Ala-OBn (29) and ME-o in case of Z-D-Glu-OBn (30) gave Z-D-Ala-Gly-NH$_2$ (37, 86%) and Z-D-Glu-Gly-NH$_2$ (38, 74%), respectively, in very high yields. Probably, the CMMs recognized D-amino acids in a different manner from L-amino acids, i.e., the carbobenzoxy group of α-position seems to bind the S$_1$ pocket. On the other hand, repulsion between the phenylmethyl group of Z-D-Phe-OBn (28), which had the biggest substituent among the three kinds of substrate, and the other parts in the pocket of active site of the MEs could cause low reactivity of Z-D-Phe-OBn (28).

In spite of their small S$_1$' pocket, all selected MEs were also applicable to the coupling of L-amino acids with an α-branched acyl acceptor, L-alaninamide (32). Although the WT enzyme could accept L-alaninamide (32) as acyl acceptor only in the case of Z-L-Phe-OBn (25) as an acyl donor, the MEs also catalyzed the reactions in the cases of not only Z-L-Phe-OBn (25) but also Z-L-Ala-OBn (26) and Z-L-Glu-OMe (27) to afford the corresponding dipeptides Z-L-Phe-L-Ala-NH$_2$ (39), Z-L-Ala-L-Ala-NH$_2$ (40), and Z-L-Glu-L-Ala-NH$_2$ (41), respectively. In the case of Z-L-Ala-OBn (26), mainly competitive hydrolysis of the esters was observed (the best was 21% by using ME-m). These results represented a dramatic improvement of the specificity of WT. The yields of the coupling of Z-L-Glu-OMe (27) with Ala-NH$_2$ (32) were as good as those of Gly-NH$_2$ (31) as acyl acceptor, and using ME-j gave the best result (64%). Although not wishing to be bound by theory, it is speculated that the strong interaction between the carboxyl group of Z-L-Glu-OMe (27) and the side chain of S166C site of MEs provides a more stable ES-complex, which could not be easily attacked by water, therefore Z-L-Glu-L-Ala-NH$_2$ (41) could be obtained in good yield.

Dipeptides Produced

Z-L-Phe-Gly-NH$_2$ (33): $^1$H NMR (DMSO-d$_6$) δ2.74 (dd, J=11.0, 14.0 Hz, 1H, CH$_2$Ph), 3.04 (dd, J=4.0, 14.0 Hz, 1H, CH$_2$Ph), 3.59–3.72 (m, 2H, NHCH$_2$CO), 4.21–4.35 (m, 1H, NHCHCO), 4.93 (d, J=12.5 Hz, 1H, OCH$_2$Ph), 4.94 (d, J=12.5 Hz, 1H), OCH$_2$Ph), 7.12 (brs, 2H, NH), 7.16–7.38 (m, 5H, Ph), 7.60 (d, J=8.5 Hz, 1H, NH), 8.27 (t, J=5.5 Hz, 1$^1$H, NH); $^{13}$C NMR (DMSO-d$_6$) δ37.3, 42.0, 56.3, 65.3, 126.3, 127.5, 127.8, 128.1, 128.4, 129.3, 137.0, 138.2, 156.0, 170.8, 171.8; HRMS (FAB$^+$) calcd for C$_{19}$H$_{22}$N$_3$O$_4$ (M+H)$^+$356.1610, found 356.1639; [α]$^{21}_D$=−3.94 (c 1.04, MeOH).

Z-L-Ala-Gly-NH$_2$ (34): $^1$H NMR (DMSO-d$_6$) δ1.20 (d, J=7.0 Hz, 3H, CH$_3$), 3.60 (dd, J=5.5, 16.0 Hz, 1H, CH$_2$NH), 3.62 (dd, J=5.5, 16.0 Hz, 1H, CH$_2$NH), 4.03 (dq, J=7.0, 7.0 Hz, 1H, CH$_3$CHNH), 5.00 (d, J=12.5 Hz, $^1$H, OCH$_2$Ph), 5.03 (d, J=12.5 Hz, 1H, OCH$_2$Ph), 7.11 (brs, 1H, NH$_2$), 7.18 (brs., 1H, NH$_2$), 7.27–7.42 (m, 5H, Ph), 7.57 (d, J=7.0 Hz, 1H, NH), 8.11 (t, J=5.5 Hz, 1H, NH); $^{13}$C NMR (DMSO-d$_6$) δ17.9, 42.0, 50.3, 65.5, 127.85, 127.89, 128.4, 136.9, 155.9, 170.9, 172.7; HRMS (FAB$^+$)calcd for C$_{13}$H$_{18}$N$_3$O$_4$ (M+H)$^+$280.1297, found 280.1307; [α]$^{25}_D$=−8.44 (c 0.64, MeOH).

Z-L-Glu-Gly-NH$_2$ (35): $^1$H NMR (DMSO-d$_6$) δ1.66–1.79 (m, 1 H, CH,CH$_2$COOH), 1.83–1.95 (m, 1H, CH$_2$CH$_2$COOH), 2.26 (t,J=7.5 Hz, 2H, CH$_2$COOH), 3.62 (d, J=5.5 Hz, 2H, NHCH$_2$CO), 3.95–4.05 (m, 1H, NHCHCO), 5.01 (d, J=12.5 Hz, 1H, OCH$_2$Ph), 5.03 (d, J=12.5 Hz, 1H, OCH$_2$Ph), 7.07 (brs, 1H, NH), 7.20 (brs, 1H, NH), 7.25–7.40 (m, 5H, Ph), 7.55 (d, J=7.5 Hz, 1H, NH), 8.11 (t, J=5.5 Hz, 1H, NH); 12.20 (brs, 1H, COOH); $^{13}$C NMR (DMSO d$_6$) δ27.0, 30.2, 41.9, 54.1, 65.6, 127.8, 127.9, 128.4, 136.9, 156.2, 170.8, 171.7, 174.0; HRMS (FAB$^+$)calcd for C$_{15}$H$_{20}$N$_3$O$_6$ (M+H)$^+$338.1352, found 338.1364; [α]$^{25}_D$=−9.28 (c 0.69, MeOH).

Z-D-Phe-Gly-NH$_2$ (36): HRMS calcd for C$_{19}$H$_{22}$N$_3$O$_4$ (M+H)$^+$356.1610, found 356.1592; [α]$^{21}_D$=+3.42 (c 1.17, MeOH).

Z-D-Ala-Gly-NH$_2$ (37): HRMS calcd for C$_{13}$H$_{18}$N$_3$O$_4$ (M+H)$^+$280.1297, found 280.1303; [α]$^{24}_D$=+8.49 (c 0.86, MeOH)

Z-D-Glu-Gly-NH$_2$ (38): HRMS calcd for C$_{15}$H$_{20}$N$_3$O$_6$ (M+H)$^+$338.1352, found 338.1353; [α]$^{24}_D$=+9.07 (c 1.08, MeOH)

Z-L-Phe-L-Ala-NH$_2$ (39): $^1$H NMR (DMSO-d$_6$) δ1.22 (d, J=7.0 Hz, 3H, CH$_3$), 2.71 (dd,J=13.5, 13.5 Hz, 1H, CH$_2$Ph), 3.03 (dd,J=3.5 , 13.5 Hz, 1H, CH$_2$Ph), 4.18–4.31 (m, 2H, NHCHCO×2), 4.93 (s, 2H, OCH$_2$Ph), 7.04 (brs, 1H, NH), 7.14–7.22 (m, 1H, NH), 7.55 (d, J=8.5 Hz, 1H, NH), 8.08 (d, J=7.5 Hz, 1H, NH); $^{13}$C NMR (DMSO-d$_6$) δ18.5, 37.4, 48.1, 56.2, 65.2, 126.3, 127.4, 127.7, 128.1, 128.4, 129.3, 137.1, 138.2, 155.9, 171.1, 174.1; HRMS (FAB$^+$) calcd for C$_{20}$H$_{24}$N$_3$O$_4$ (M+H)$^+$370.1767, found 370.1769; [α]$^{24}_D$=−8.86 (c 0.44, MeOH).

Z-L-Ala-L-Ala-NH$_2$ (40): $^1$H NMR (DMSO-d$_6$) δ1.19 (d, J=7.0 Hz, 3H, CH$_3$), 1.24 (d, J=7.5 Hz, 3H, CH$_3$), 3.90–4.26 (m, 2H, NHCHCO×2), 5.01 (s, 2H, CH$_2$OPh), 7.02 (brs, 1H, NH), 7.13 (brs, 1H, NH), 7.25–7.45 (m, 5H, Ph), 7.51 (d, J=6.5 Hz, 1H, NH), 7.88 (d, J=7.5 Hz, 1H, NH); $^{13}$C NMR (DMSO-d$_6$) δ18.1, 18.5, 47.9, 50.2, 65.4, 127.78, 127.84, 128.4, 137.1, 155.8, 172.0, 174.2; HRMS (FAB$^+$)calcd for C$_{14}$H$_{20}$N$_3$O$_4$ (M+H)$^+$294.1454, found 294.1457; [α]$^{21}_D$=−20.4 (c 0.77, MeOH).

Z-L-Glu-L-Ala-NH$_2$ (41): $^1$H NMR (DMSO-d$_6$) δ1.20 (d, J=8.0 Hz, 3H, CH$_3$), 1.68–1.82 (m, 1H, CH$_2$CH$_2$COOH), 1.82–2.03 (m, 1H, CH$_2$CH$_2$COOH), 2.21–2.40 (m, 2H, CH$_2$CH$_2$COOH), 3.93–4.25 (m, 2H, NHCHCO×2), 5.02 (s, 2H, OCH$_2$Ph), 7.02 (brs, 1H, NH), 7.18–7.46 (m, 5H, Ph), 7.54 (dd, J=7.5, 24.0 Hz, 2H, NH$_2$), 7.92 (d, J=7.5 Hz, 1H, NH), 12.40 (brs, 1H, COOH); $^{13}$C NMR (DMSO-d$_6$) δ18.4, 26.2, 30.3, 48.0, 53.1, 65.4, 127.0, 127.7, 127.8, 127.9, 128.4, 129.3, 137.0, 156.2, 173.7, 173.8, 174.1; HRMS (FAB$^+$) calcd for C$_{16}$H$_{22}$N$_3$O$_6$ (M+H)$^+$ 352.1509, found 352.1502; [α]$^{25}_D$==16.7 (c 0.76, MeOH).

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A modified subtilisin enzyme having esterase and amidase activities, said modified enzyme comprising a cysteine residue substituted for an amino acid residue selected from the group consisting of residues 62, 166, 217 and 222, wherein said amino acid residue is numbered according to its equivalent in the amino acid sequence of *Bacillus amyloliquefaciens* subtilisin BPN' (SEQ ID NO: 2), and wherein said cysteine residue is modified by replacing the thiol hydrogen in the Cysteine residue with a thiol side chain selected from the group consisting of —SCH$_3$, —SCH$_2$CH$_3$, —SCH$_2$CH(CH$_3$)$_2$, —S(CH$_2$)$_4$CH$_3$, —S(CH$_2$)$_5$CH$_3$, —S(CH$_2$)$_9$CH$_3$, —SCH$_2$C$_6$H$_5$, —SCH$_2$CH$_2$NH$_3^+$, —SCH$_2$CH$_2$SO$_3^-$, —SCH$_2$(p-COOH—C$_6$H$_4$), and —SCH$_2$C$_6$F$_5$ to form the modified enzyme.

2. A modified enzyme according to claim 1, wherein the esterase activity is from about 350s$^{-1}$ mM$^{-1}$ to about 11100s$^{-1}$ mM$^{-1}$.

3. A modified enzyme according to claim 1, wherein the amidase activity is from about 5.6s$^{-1}$ mM$^{-1}$ to about 355s$^{-1}$ mM$^{-1}$.

4. A detergent additive comprising the modified enzyme of claim 1.

5. A feed additive comprising the modified enzyme of claim 1.

6. The modified enzyme of claim 1, wherein the cysteine residue is substituted for residue 62, and wherein the thiol side chain is selected from the group consisting of —SCH$_3$, —SCH$_2$CH$_3$, —SCH$_2$CH(CH$_3$)$_2$, —S(CH$_2$)$_4$CH$_3$, —S(CH$_2$)$_5$CH$_3$, —SCH$_2$CH$_2$NH$_3^+$, and —SCH$_2$CH$_2$SO$_3^+$.

7. The modified enzyme of claim 6, wherein the thiol side chain is —SCH$_3$.

8. The modified enzyme of claim 6, wherein the thiol side chain is —SCH$_2$CH$_3$.

9. The modified enzyme of claim 6, wherein the thiol side chain is —SCH$_2$CH$_2$NH$_3^+$.

10. The modified enzyme of claim 6, wherein the thiol side chain is —SCH$_2$CH$_2$SO$_3^+$.

11. The modified enzyme of claim 1, wherein the cysteine residue is substituted for residue 166, and wherein the thiol side chain is selected from the group consisting of —SCH$_3$, —SCH$_2$C$_6$H$_5$, —SCH$_2$CH$_2$NH$_3^+$, and —SCH$_2$CH$_2$SO$_3^-$, —SCH$_2$(p-COOH—C$_6$H$_4$), and —SCH$_2$C$_6$F$_5$.

12. The modified enzyme of claim 11, wherein the thiol side chain is —SCH$_2$C$_6$H$_5$.

13. The modified enzyme of claim 11, wherein the thiol side chain is —SCH$_2$(p-COOH—C$_6$H$_4$).

14. The modified enzyme of claim 11, wherein the thiol side chain is —SCH$_2$C$_6$F$_5$.

15. The modified enzyme of claim 1, wherein the cysteine residue is substituted for residue 217, and wherein the thiol side chain is selected from the group consisting of —SCH$_3$, —SCH$_2$CH$_3$, —SCH$_2$CH(CH$_3$)$_2$, —S(CH$_2$)$_4$CH$_3$, —S(CH$_2$)$_5$CH$_3$, —SCH$_2$CH$_2$NH$_3^+$, and —SCH$_2$CH$_2$SO$_3^-$.

16. The modified enzyme of claim 15, wherein the thiol side chain is —SCH$_2$CH$_2$NH$_3^+$.

17. The modified enzyme of claim 15, wherein the thiol side chain is —SCH$_2$CH$_2$SO$_3^-$.

18. The modified enzyme of claim 1, wherein the cysteine residue is substituted for residue 222, and wherein the thiol side chain is —SCH$_2$CH$_2$NH$_3^+$.

19. The modified enzyme of claim 1, wherein said subtilisin is subtilisin *Bacillus lentus*.

* * * * *

UNITED STATES PATENT AND TRADEMARK OFFICE
CERTIFICATE OF CORRECTION

PATENT NO. : 6,395,532 B1
DATED : May 28, 2002
INVENTOR(S) : J. Bryan Jones

It is certified that error appears in the above-identified patent and that said Letters Patent is hereby corrected as shown below:

Column 30,
Line 7, please add sequence to end of claim -- (SEQ. ID NO: 1). --

Signed and Sealed this

Thirteenth Day of April, 2004

JON W. DUDAS
*Acting Director of the United States Patent and Trademark Office*